United States Patent
Hashimoto et al.

(10) Patent No.: US 9,884,061 B2
(45) Date of Patent: Feb. 6, 2018

(54) INJECTION PREPARATION AND METHOD FOR PRODUCING SAME

(71) Applicant: FUJIFILM CORPORATION, Minato-ku, Tokyo (JP)

(72) Inventors: Shinichi Hashimoto, Kanagawa (JP); Shigetomo Tsujihata, Kanagawa (JP); Yasuyuki Izumi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 15/084,486

(22) Filed: Mar. 30, 2016

(65) Prior Publication Data

US 2016/0243123 A1    Aug. 25, 2016

Related U.S. Application Data

(63) Continuation of application No. PCT/JP2014/076456, filed on Oct. 2, 2014.

(30) Foreign Application Priority Data

| Oct. 3, 2013 | (JP) | ................................ 2013-208351 |
| Nov. 28, 2013 | (JP) | ................................ 2013-246565 |
| Mar. 31, 2014 | (JP) | ................................ 2014-072126 |

(51) Int. Cl.

| A61K 31/519 | (2006.01) |
| A61K 9/08 | (2006.01) |
| A61K 9/00 | (2006.01) |
| A61K 47/12 | (2006.01) |
| A61K 47/20 | (2006.01) |
| A61K 47/22 | (2006.01) |
| B65B 3/00 | (2006.01) |
| B65B 31/00 | (2006.01) |

(52) U.S. Cl.
CPC .......... *A61K 31/519* (2013.01); *A61K 9/0019* (2013.01); *A61K 9/08* (2013.01); *A61K 47/12* (2013.01); *A61K 47/20* (2013.01); *A61K 47/22* (2013.01); *B65B 3/003* (2013.01); *B65B 31/00* (2013.01)

(58) Field of Classification Search
CPC .................................................. A61K 31/519
See application file for complete search history.

(56) References Cited

U.S. PATENT DOCUMENTS

| 2003/0216416 A1 | 11/2003 | Reutzel-Eden et al. |
| 2015/0297724 A1 | 10/2015 | Park et al. |

FOREIGN PATENT DOCUMENTS

| EP | 2995298 A1 | 3/2016 |
| JP | 2003-521518 A | 7/2003 |
| JP | 2003-530321 A | 10/2003 |
| JP | 2014-237607 A | 12/2014 |
| JP | 2016-500099 A | 1/2016 |
| KR | 101260636 B1 | 5/2013 |
| WO | 01/56575 A1 | 8/2001 |
| WO | 2010/030598 A2 | 3/2010 |
| WO | 2012/015810 A2 | 2/2012 |
| WO | 2012/121523 A2 | 9/2012 |
| WO | 2013/179248 A1 | 12/2013 |
| WO | 2014/084651 A1 | 6/2014 |

OTHER PUBLICATIONS

Extended European Search Report dated Nov. 7, 2016, issued in corresponding EP Patent Application.
Submission of Publications, Submitted by third party on Jan. 30, 2017, received by Applicant on Feb. 21, 2017, for corresponding JP Application No. 2015-540559 and a Partial English Translation thereof.
Antioxidants and Other Micronutrients in Complementary Oncology, from the Academy of Micronutrient Medicine, Essen, Germany, published online Feb. 20, 2009.
English language translation of the following: Office action dated May 26, 2017 from the SIPO in a Chinese patent application No. 201480054539.3 corresponding to the instant patent application. This office action translation is submitted now in order to supplement the understanding of the cited reference which is being disclosed in the instant Information Disclosure Statement.
English language translation of the following: Office action dated Feb. 28, 2017 from the JPO in a Japanese patent application No. 2015-540559 corresponding to the instant patent application. This office action translation is submitted now in order to supplement the understanding of the cited references which are being disclosed in the instant Information Disclosure Statement.
English language translation of the following: Office action dated Dec. 5, 2017 from the JPO in a Japanese patent application No. 2015-540559 corresponding to the instant patent application.

*Primary Examiner* — Noble Jarrell
*Assistant Examiner* — John S Kenyon
(74) *Attorney, Agent, or Firm* — Solaris Intellectual Property Group, PLLC

(57) ABSTRACT

Provided are an injection preparation which include: an aqueous composition containing pemetrexed or a salt thereof, at least one antioxidant agent which is selected from the group consisting of ascorbic acid, an ascorbic acid derivative, and salts thereof, and the content of which is 0.0001 mass % to 0.5 mass % with respect to the total mass of the aqueous composition in terms of ascorbic acid, and an aqueous solvent of greater than or equal to 50 mass % with respect to the total mass of the aqueous composition; and a container which encloses the aqueous composition, in which the concentration of oxygen in gas within the container which encloses the aqueous composition is less than or equal to 0.2 volume %, and a method for producing the injection preparation.

12 Claims, No Drawings

INJECTION PREPARATION AND METHOD FOR PRODUCING SAME

CROSS-REFERENCE TO RELATED APPLICATIONS

This application is a continuation application of International Application No. PCT/JP2014/076456, filed Oct. 2, 2014, the disclosure of which is incorporated herein by reference in its entirety. Further, this application claims priority from Japanese Patent Application No. 2013-208351, filed Oct. 3, 2013, Japanese Patent Application No. 2013-246565, filed Nov. 28, 2013, and Japanese Patent Application No. 2014-072126, filed Mar. 31, 2014, the disclosures of which are incorporated herein by reference in their entirety.

BACKGROUND OF THE INVENTION

1. Field of the Invention

The present invention relates to an injection preparation and a method for producing the same.

2. Description of the Related Art

Pemetrexed is a type of active ingredient of an anti-tumor therapeutic agent, and an anticancer agent which contains pemetrexed as an active ingredient is administered to a patient through intravenous drip.

In JP2003-521518A, there is a disclosure of a liquid preparation obtained by combining at least one antioxidant agent, which is selected from the group consisting of monothioglycerol, L-cysteine, and thioglycolic acid, with pemetrexed.

In WO2012/015810A, there is a disclosure of a composition at a pH of 8 to 9.5 which is obtained by combining at least one antioxidant agent which is selected from the group consisting of lipoic acid, dihydrolipoic acid, and methionine, at least one chelating agent which is selected from the group consisting of lactobionic acid and sodium citrate, and a pharmaceutically acceptable liquid, with pemetrexed.

In WO2012/121523A, there is a disclosure of producing an injection agent by adjusting the concentration of dissolved oxygen in an injection solution which contains pemetrexed, but does not contain an antioxidant agent to be less than or equal to 1 ppm, and by adjusting the concentration of oxygen while filling an injection container with the injection solution to be less than or equal to 0.2%.

SUMMARY OF THE INVENTION

As described above, an anticancer agent containing pemetrexed as an active ingredient is administered to a patient through intravenous drip. For this reason, the development of an aqueous composition containing pemetrexed in which convenience and safety is considered when in use is desired.

For this reason, various examinations have been performed. However, in methods disclosed in JP2003-521518A, WO2012/015810A, or WO2012/121523A, it became clear that preservation stability of pemetrexed contained in a prepared aqueous composition or a salt thereof is insufficient.

In such a situation, development of a preparation, in which the preservation stability can be further improved in an aqueous composition of pemetrexed or a salt thereof, is desired.

An object of the present invention is to provide an injection preparation which can improve preservation stability of pemetrexed or a salt thereof, and a method for producing the same.

Means for solving the problem is as follows.

<1> An injection preparation including:

an aqueous composition containing the following (i) to (iii); and a container which encloses the aqueous composition, in which the concentration of oxygen in gas within the container which encloses the aqueous composition is less than or equal to 0.2 volume %:

(i) pemetrexed or a salt thereof;

(ii) at least one antioxidant agent which is selected from the group consisting of ascorbic acid, an ascorbic acid derivative, and salts thereof, and the content of which is 0.0001 mass % to 0.5 mass % with respect to the total mass of the aqueous composition in terms of ascorbic acid; and (iii) an aqueous solvent of greater than or equal to 50 mass % with respect to the total mass of the aqueous composition.

<2> An injection preparation including:

an aqueous composition; and a container which encloses the aqueous composition, in which the aqueous composition contains the following (i) to (iii), and in which the ratio of the number of oxygen molecules with respect to the number of pemetrexed molecules in the injection preparation is less than or equal to 0.0025:

(i) pemetrexed or a salt thereof;

(ii) at least one antioxidant agent which is selected from the group consisting of ascorbic acid, an ascorbic acid derivative, and salts thereof, and the content of which is 0.0001 mass % to 0.5 mass % with respect to the total mass of the aqueous composition in terms of ascorbic acid; and (iii) an aqueous solvent of greater than or equal to 50 mass % with respect to the total mass of the aqueous composition.

<3> The injection preparation according to <1> or <2>, in which the content of the antioxidant agent is 0.0001 mass % to 0.1 mass % with respect to the total mass of the aqueous composition.

<4> The injection preparation according to any one of <1> to <3>, in which the content of the antioxidant agent is 0.001 mass % to 0.1 mass % with respect to the total mass of the aqueous composition.

<5> The injection preparation according to any one of <1> to <4>, in which the content of the antioxidant agent is 0.001 mass % to 0.05 mass % with respect to the total mass of the aqueous composition.

<6> The injection preparation according to any one of <1> to <5>, in which the pH of the aqueous composition is higher than 5.5.

<7> The injection preparation according to any one of <1> to <6>, in which the aqueous composition further contains at least one pH modifier selected from the group consisting of hydrochloric acid, sodium hydroxide, phosphoric acid or a salt thereof, citric acid or a salt thereof, triethanolamine, trometamol, and disodium edetate.

<8> The injection preparation according to <7>, in which the pH modifier is at least one selected from the group consisting of citric acid or a salt thereof.

<9> A method for producing an injection preparation, including:
  producing an aqueous composition which contains:
  (i) pemetrexed or a salt thereof,
  (ii) at least one antioxidant agent which is selected from the group consisting of ascorbic acid, an ascorbic acid derivative, and salts thereof, and the content of which is 0.0001 mass % to 0.5 mass % with respect to the total mass of the aqueous composition in terms of ascorbic acid, and
  (iii) an aqueous solvent of greater than or equal to 50 mass % with respect to the total mass of the aqueous composition; and
  filling the container with the aqueous composition under an inert gas atmosphere or substituting gas within a container with inert gas after filling the container with the aqueous composition.

<10> The production method according to <9>,
  in which the inert gas is nitrogen.

<11> An injection preparation including:
  an aqueous composition containing the following (i) to (iv); and
  a container which encloses the aqueous composition,
  in which the concentration of oxygen in gas within the container which encloses the aqueous composition is less than or equal to 1.5 volume %:
  (i) pemetrexed or a salt thereof;
  (ii) at least one antioxidant agent A which is selected from the group consisting of ascorbic acid, an ascorbic acid derivative, and salts thereof, and the content of which is 0.001 mass % to 1.0 mass % with respect to the total mass of the aqueous composition in terms of ascorbic acid;
  (iii) at least one antioxidant agent B which is selected from the group consisting of a compound having a thiol group or a salt thereof, and a compound having a sulfide bond or a salt thereof, and the content of which is 0.0005 mass % to 0.1 mass % with respect to the total mass of the aqueous composition; and
  (iv) an aqueous solvent of greater than or equal to 50 mass % with respect to the total mass of the aqueous composition.

<12> An injection preparation including:
  an aqueous composition; and
  a container which encloses the aqueous composition,
  in which the aqueous composition contains the following (i) to (iv), and
  in which the ratio of the number of oxygen molecules with respect to the number of pemetrexed molecules in the injection preparation is less than or equal to 0.0120:
  (i) pemetrexed or a salt thereof;
  (ii) at least one antioxidant agent A which is selected from the group consisting of ascorbic acid, an ascorbic acid derivative, and salts thereof, and the content of which is 0.001 mass % to 1.0 mass % with respect to the total mass of the aqueous composition in terms of ascorbic acid;
  (iii) at least one antioxidant agent B which is selected from the group consisting of a compound having a thiol group or a salt thereof, and a compound having a sulfide bond or a salt thereof, and the content of which is 0.00050 mass % to 0.15 mass % with respect to the total mass of the aqueous composition; and
  (iv) an aqueous solvent of greater than or equal to 50 mass % with respect to the total mass of the aqueous composition.

<13> The injection preparation according to <11> or <12>,
  in which the antioxidant agent B is a compound having a thiol group or a salt thereof.

<14> The injection preparation according to any one of <11> to <13>,
  in which the compound having a thiol group or a salt thereof is at least one selected from the group consisting of cysteine or a salt thereof, thioglycerol, and thioglycolic acid or a salt thereof.

<15> The injection preparation according to any one of <11> to <14>,
  in which the compound having a thiol group or a salt thereof is cysteine or a salt thereof <16> The injection preparation according to any one of <11> to <15>,
  in which the compound having a thiol group or a salt thereof includes cysteine or a salt thereof, and thioglycerol.

<17> The injection preparation according to any one of <11> to <16>,
  in which the content of the antioxidant agent A is 0.005 mass % to 0.5 mass % with respect to the total mass of the aqueous composition.

<18> The injection preparation according to any one of <11> to <17>,
  in which the content of the antioxidant agent B is 0.0050 mass % to 0.15 mass % with respect to the total mass of the aqueous composition.

<19> The injection preparation according to any one of <11> to <18>,
  in which the ratio of the content of the antioxidant agent B to the content of the antioxidant agent A (antioxidant agent A:antioxidant agent B) is 1:0.05 to 1:10 on a mass basis.

<20> The injection preparation according to any one of <11> to <19>,
  in which the pH of the aqueous composition is higher than 5.5 and lower than or equal to 9.5.

<21> The injection preparation according to any one of <11> to <20>,
  in which the aqueous composition contains at least one pH modifier selected from the group consisting of hydrochloric acid, sodium hydroxide, phosphoric acid or a salt thereof, citric acid or a salt thereof, triethanolamine, trometamol, and disodium edetate.

<22> The injection preparation according to <21>,
  in which the pH modifier is at least one selected from citric acid or a salt thereof.

<23> A method for producing an injection preparation, including:
  producing an aqueous composition which contains:
  (i) pemetrexed or a salt thereof,
  (ii) at least one antioxidant agent A which is selected from the group consisting of ascorbic acid, an ascorbic acid derivative, and salts thereof, and the content of which is 0.001 mass % to 1.0 mass % with respect to the total mass of the aqueous composition in terms of ascorbic acid,
  (iii) at least one antioxidant agent B which is selected from the group consisting of a compound having a thiol group or a salt thereof, and a compound having a sulfide bond or a salt thereof, and the content of which is 0.00050 mass % to 0.15 mass % with respect to the total mass of the aqueous composition, and
  (iv) an aqueous solvent of greater than or equal to 50 mass % with respect to the total mass of the aqueous composition; and
  filling the container with the aqueous composition under an inert gas atmosphere or substituting gas within a container with inert gas after filling the container with the aqueous composition.

<24> The production method according to <23>,
  in which the inert gas is nitrogen.

According to the present invention, it is possible to provide an injection preparation and a method for producing the same which can improve preservation stability of pemetrexed or a salt thereof, and a method for producing the same.

DESCRIPTION OF THE PREFERRED EMBODIMENTS

Hereinafter, an injection preparation of the present invention will be described in details.

In the present specification, the numerical range represented by "to" represents a range including numerical values denoted before and after "to" as a lower limit value and an upper limit value.

In the present specification, in a case where there are a plurality of substances corresponding to the respective components in a composition, the amount of each of the components in the composition means a total amount of the plurality of substances existing in the composition unless otherwise specified.

In the present specification, the term "step" is not only an independent step, but a case where a step cannot be clearly distinguished from other steps is also included to this term as long as an expected purpose of the step can be achieved.

In the present invention, the preservation stability means that suppression of decomposition of pemetrexed or a salt thereof is stably maintained, and suppression of coloration of an injection preparation caused by presence of a decomposition product of pemetrexed or a salt thereof is stably maintained, when the injection preparation is preserved.

A first aspect of an injection preparation of the present invention includes: an aqueous composition containing (i) pemetrexed or a salt thereof, (ii) at least one antioxidant agent which is selected from the group consisting of ascorbic acid, an ascorbic acid derivative, and salts thereof, and the content of which is 0.0001 mass % to 0.5 mass % with respect to the total mass of the aqueous composition in terms of ascorbic acid, and (iii) an aqueous solvent of greater than or equal to 50 mass % with respect to the total mass of the aqueous composition; and a container which encloses the aqueous composition. The concentration of oxygen in gas within the container which encloses the aqueous composition is less than or equal to 0.2 volume %.

In addition, the first aspect of the injection preparation of the present invention includes an injection preparation including an aqueous composition and a container which encloses the aqueous composition, in which the aqueous composition contains (i) pemetrexed or a salt thereof, (ii) at least one antioxidant agent which is selected from the group consisting of ascorbic acid, an ascorbic acid derivative, and salts thereof, and the content of which is 0.0001 mass % to 0.5 mass % with respect to the total mass of the aqueous composition in terms of ascorbic acid, and (iii) an aqueous solvent of greater than or equal to 50 mass % with respect to the total mass of the aqueous composition, and in which the ratio of the number of oxygen molecules with respect to the number of pemetrexed molecules in the injection preparation is less than or equal to 0.0025.

The injection preparation of the present invention can improve preservation stability of pemetrexed or a salt thereof in the aqueous composition by containing at least one antioxidant agent which is selected from the group consisting of ascorbic acid, an ascorbic acid derivative, and salts thereof, and the content of which is 0.0001 mass % to 0.5 mass % with respect to the total mass of the aqueous composition in terms of ascorbic acid, and by making the concentration of oxygen within the container which encloses the aqueous composition be less than or equal to 0.2 volume %.

Particularly, in JP2003-521518A (above-described Patent Document 1), in a case where the present invention is combined with pemetrexed or a salt thereof, the present invention can exhibit an unexpected effect in which it is possible to improve preservation stability of pemetrexed or a salt thereof in the aqueous composition using ascorbic acid, which is an antioxidant agent and is considered that it is impossible to exhibit the effect of the preservation stability, within a range of a low concentration being 0.0001 mass % to 0.5 mass %.

A second aspect of an injection preparation of the present invention includes an injection preparation including: an aqueous composition containing (i) pemetrexed or a salt thereof, (ii) at least one antioxidant agent A which is selected from the group consisting of ascorbic acid, an ascorbic acid derivative, and salts thereof, and the content of which is 0.001 mass % to 1.0 mass % with respect to the total mass of the aqueous composition in terms of ascorbic acid, (iii) at least one antioxidant agent B which is selected from the group consisting of a compound having a thiol group or a salt thereof, and a compound having a sulfide bond or a salt thereof, and the content of which is 0.00050 mass % to 0.15 mass % with respect to the total mass of the aqueous composition, and (iv) an aqueous solvent of greater than or equal to 50 mass % with respect to the total mass of the aqueous composition; and a container which encloses the aqueous composition, in which the concentration of oxygen in gas within the container which encloses the aqueous composition is less than or equal to 1.5 volume %.

In addition, the second aspect of the injection preparation of the present invention includes an injection preparation including an aqueous composition and a container which encloses the aqueous composition, in which the aqueous composition contains (i) pemetrexed or a salt thereof, (ii) at least one antioxidant agent A which is selected from the group consisting of ascorbic acid, an ascorbic acid derivative, and salts thereof, and the content of which is 0.001 mass % to 1.0 mass % with respect to the total mass of the aqueous composition in terms of ascorbic acid, (iii) at least one antioxidant agent B which is selected from the group consisting of a compound having a thiol group or a salt thereof, and a compound having a sulfide bond or a salt thereof, and the content of which is 0.0005 mass % to 0.1 mass % with respect to the total mass of the aqueous composition, and (iv) an aqueous solvent of greater than or equal to 50 mass % with respect to the total mass of the aqueous composition, and in which the ratio of the number of oxygen molecules with respect to the number of pemetrexed molecules in the injection preparation is less than or equal to 0.0120.

The injection preparation of the present invention can improve preservation stability of pemetrexed or a salt thereof in the aqueous composition by containing at least one antioxidant agent which is selected from the group consisting of ascorbic acid, an ascorbic acid derivative, and salts thereof, and the content of which is 0.0001 mass % to 0.5 mass % with respect to the total mass of the aqueous composition in terms of ascorbic acid, and by making the ratio of the number of oxygen molecules with respect to the number of pemetrexed molecules in the injection preparation be less than or equal to 0.0025 in the injection preparation of the first aspect and be less than or equal to 0.0120 in the injection preparation of the second aspect.

Hereinafter, the aqueous composition according to the first aspect of the injection preparation of the present invention is simply called an "aqueous composition", the injection preparation according to the first aspect is simply called an "injection preparation", the aqueous composition according to the second aspect is called a "second aqueous composition", and the injection preparation according to the second aspect is called a "second injection preparation".

The second injection preparation of the present invention can exhibit an unexpected effect in which it is possible to suppress coloration of the second aqueous composition by combining a specific amount of the antioxidant agent B with at least one antioxidant agent A which is selected from the group consisting of ascorbic acid, an ascorbic acid derivative, and salts thereof, and the content of which is 0.001 mass % to 1.0 mass % with respect to the total mass of the second aqueous composition in terms of ascorbic acid, and by making the concentration of oxygen in gas within the container which encloses the second aqueous composition be less than or equal to 1.5 volume %. Particularly, even in a case where the concentration of oxygen in gas within the container which encloses the second aqueous composition becomes higher than 0.2 volume %, the present invention can exhibit an unexpected effect which can suppress coloration of the second aqueous composition itself by combining a specific amount of the antioxidant agent A and a specific amount of the antioxidant agent B.

In addition, the second injection preparation according to the present invention can exhibit the effect of suppressing the coloration of the second aqueous composition and suppressing decomposition of pemetrexed or a salt thereof which is contained in the second aqueous composition, by combining the antioxidant agent B with the antioxidant agent A even without strictly adjusting the content of the antioxidant agent A to be less than or equal to 0.5 mass %.

<Aqueous Composition>

The aqueous composition according to the present invention contains (i) pemetrexed or a salt thereof, (ii) at least one antioxidant agent which is selected from the group consisting of ascorbic acid, an ascorbic acid derivative, and salts thereof, and the content of which is 0.0001 mass % to 0.5 mass % with respect to the total mass of the aqueous composition in terms of ascorbic acid, and (iii) an aqueous solvent of greater than or equal to 50 mass % with respect to the total mass of the aqueous composition.

In addition, the aqueous composition may contain other components as necessary.

(Pemetrexed or Salt Thereof)

The aqueous composition according to the present invention contains pemetrexed or a salt thereof.

Pemetrexed is an active ingredient of Alimta (registered trademark) which is produced and sold as an antimetabolitic anti-malignant tumor agent by Eli Lilly Japan K. K.

As the salt of pemetrexed, any pharmaceutically acceptable salt may be used. Examples thereof include a salt of pemetrexed and alkali metal, a salt of pemetrexed and alkali earth metal, a salt of pemetrexed and transition metal, and a salt of pemetrexed and basic ammonium.

Specific examples thereof include an alkali metal salt with sodium, potassium, or the like; an alkaline earth metal salt with calcium, magnesium, or the like; a transition metal salt with zinc, iron, cobalt, copper, or the like; and a basic ammonium salt with ammonia, triethanolamine, L-histidine, L-arginine, L-lysine, or the like.

Among these, a sodium salt or a potassium salt is preferable.

In pemetrexed or a salt thereof, a hydrate thereof is also included.

Pemetrexed or a salt thereof can be generally used alone, or two or more kinds thereof can also be used in combination.

The concentration of pemetrexed or a salt thereof in an aqueous composition is preferably 1.0 mg/mL to 100.0 mg/mL, more preferably 5.0 mg/mL to 50.0 mg/mL, and still more preferably 10.0 mg/mL to 37.5 mg/mL, from the viewpoint of solubility and medicinal effect of pemetrexed.

(Antioxidant Agent)

The antioxidant agent contained in an aqueous composition according to the present invention is a substance which suppresses oxidative decomposition of pemetrexed in the present invention.

The aqueous composition according to the present invention contains at least one antioxidant agent which is selected from the group consisting of ascorbic acid, an ascorbic acid derivative, and salts thereof, and the content of which is 0.0001 mass % to 0.5 mass % with respect to the total mass of the aqueous composition in terms of ascorbic acid.

As the ascorbic acid, it is possible to use a commercially available product. Examples of the commercially available product include "Viscorin" (trade name) manufactured by Daiichi Fine Chemical Co., Ltd., "Vitamin C" (trade name) manufactured by Mitsubishi Tanabe Pharma Corporation, "ascorbic acid bulk powder "Takeda"" (trade name) manufactured by Takeda Pharmaceutical Company Limited, "Vitamin C" (trade name) manufactured by Towa-Kasei Co., Ltd., "Ascorbic Acid" (trade name) manufactured by BASF SE, and "Ascorbic Acid" (trade name) manufactured by DSM.

The ascorbic acid derivative is not particularly limited as long as the ascorbic acid derivative is a pharmaceutically acceptable ascorbic acid derivative. Examples thereof include ascorbic acid alkyl ester, ascorbic acid phosphate ester, ascorbic acid glucoside, and ascorbic acid alkyl ether.

More specific examples of the ascorbic acid derivative include ascorbic acid alkyl esters such as ascorbyl monostearate, ascorbyl monopalmitate, ascorbyl monoiso palmitate, ascorbyl monooleate, ascorbyl distearate, ascorbyl dipalmitate, and ascorbyl monopalmitate; ascorbic acid phosphate esters such as ascorbic acid monophosphate ester, ascorbic acid diphosphate ester, and ascorbic acid triphosphate ester; ascorbic acid monoglucosides such as ascorbic acid ethyl ether and ascorbic acid methyl ether; and ascorbic acid diglucosides such as ascorbic acid diglucoside. These ascorbic acid derivatives have a configuration with which at least one hydroxyl group at 6-position, 2-position, 3-position, and 5-position of ascorbic acid is substituted.

Among these, the ascorbic acid derivatives are preferably ascorbic acid phosphate ester, ascorbic acid glucoside, or ascorbic acid alkyl ether, and are more preferably ascorbic acid phosphate ester or ascorbic acid glucoside, As the ascorbic acid derivatives, it is possible to use commercially available product. Examples of the commercially available product include ascorbic acid 2-glucoside (trade name: Ascofresh manufactured by Hayashibara Co., Ltd.), magnesium ascorbyl phosphate (trade name: Ascorbic Acid PM manufactured by Showa Denko K. K.), and sodium ascorbyl phosphate (trade name: Ascorbic Acid PS manufactured by Showa Denko K. K.).

As the salt of the ascorbic acid or the ascorbic acid derivatives, any pharmaceutically acceptable salt may be used. Examples thereof include a salt of alkali metal and ascorbic acid or an ascorbic acid derivative, a salt of alkali earth metal and ascorbic acid or an ascorbic acid derivative, a salt of transition metal and ascorbic acid or an ascorbic acid derivative, and a salt of basic ammonium and ascorbic acid or an ascorbic acid derivative.

Specific examples thereof include an alkali metal salt with sodium, potassium, or the like; an alkaline earth metal salt with calcium, magnesium, or the like; a transition metal salt with zinc, iron, cobalt, copper, or the like; and a basic ammonium salt with ammonium, triethanolamine, L-histidine, L-arginine, L-lysine, or the like.

Among these, as the salt of ascorbic acid or an ascorbic acid derivative, sodium ascorbate, potassium ascorbate, magnesium ascorbate, calcium ascorbate, sodium ascorbyl phosphate, magnesium ascorbyl phosphate, or the like is preferable.

At least any one antioxidant agent (hereinafter, also simply called "specific antioxidant agent") selected from the group consisting of ascorbic acid, an ascorbic acid derivative, and salts thereof may be used alone, or two or more kinds thereof may be used in combination.

In addition, the specific antioxidant agent may be used by being combined with other antioxidant agents.

Examples of the other antioxidant agents include antioxidant agents based on hindered phenol such as dibutylhydroxytoluene, butylhydroxyanisole, and tocopherol, but are not limited thereto.

The content of the specific antioxidant agent contained in the aqueous composition according to the present invention is 0.0001 mass % to 0.5 mass % with respect to the total mass of the aqueous composition in terms of ascorbic acid.

In both cases where the content of the specific antioxidant agent is made to be smaller than 0.0001 mass % with respect to the total mass of the aqueous composition in terms of ascorbic acid or where the content of the specific antioxidant agent is made to be larger than 0.5 mass % with respect to the total mass of the aqueous composition in terms of ascorbic acid, preservation stability of pemetrexed or a salt thereof deteriorates, which is not preferable.

In addition, in order to further improve the preservation stability, the content of the specific antioxidant agent contained in the aqueous composition according to the present invention is preferably 0.0001 mass % to 0.1 mass %, more preferably 0.001 mass % to 0.1 mass %, and still more preferably 0.001 mass % to 0.05 mass %, with respect to the total mass of the aqueous composition in terms of ascorbic acid.

Here, the expression "in terms of ascorbic acid" means that the content of the specific antioxidant agent is calculated by employing the mass of the ascorbic acid itself with respect to the ascorbic acid and by employing the mass of a partial structure derived from ascorbic acid contained in an derivative or a salt with respect to an ascorbic acid derivative, a salt of ascorbic acid, and a salt of the ascorbic acid derivative.

In the content ratio (pemetrexed or a salt thereof: specific antioxidant agent) of the specific antioxidant agent to pemetrexed or a salt thereof in the aqueous composition according to the present invention, the ratio of the specific antioxidant agent with respect to pemetrexed or a salt thereof is extremely small. The content ratio is a ratio of employing the mass. Specifically, the content ratio (pemetrexed or a salt thereof: specific antioxidant agent) of the specific antioxidant agent to pemetrexed or a salt thereof in the aqueous composition of the present invention is preferably 5:1 to 25000:1, more preferably 25:1 to 25000:1, and still more preferably 250:1 to 5000:1, from the viewpoint of preservation stability of pemetrexed or a salt thereof.

In contrast, in some cases, in the content ratio of the specific antioxidant agent to a medicinal component in an aqueous composition in a commercial preparation, the ratio of the specific antioxidant agent with respect to the medicinal component is large. For example, the content ratio (medicinal component: specific antioxidant agent) of the specific antioxidant agent to the medicinal component in an aqueous composition "MGA Cinch Injection" as a commercial preparation is 1:33, and the content ratio (medicinal component: specific antioxidant agent) of the specific antioxidant agent to the medicinal component in an aqueous composition "ergometrine maleate" is 1:50.

(Aqueous Solvent)

Examples of the aqueous solvent according to the present invention are not particularly limited, and examples thereof include water or a solvent which is mixed with a medium that can be mixed with water. The water or the solvent which is mixed with a medium that can be mixed with water can contain arbitrary components which function as a pH modifier or the like to be described below. The aqueous solvent may be an aqueous solution containing these arbitrary components. In addition, the aqueous solvent may be a buffer solution which has a buffering capacity. Examples of the arbitrary components include organic acid, an organic base, inorganic acid, inorganic base, or salts thereof.

The aqueous composition of the present invention contains 50 mass % or more of an aqueous solvent with respect to the total mass of the aqueous composition.

The aqueous solvent is not particularly limited as long as the aqueous solvent can be used in injection preparation. Examples of the aqueous solvent include purified water for injection, a normal saline solution, a glucose solution, distilled water, ultrapure water such as Milli-Q water (the "Milli-Q" is a trade name).

The content of the aqueous solvent contained in the aqueous composition according to the present invention is greater than or equal to 50 mass % with respect to the total mass of the aqueous composition.

In addition, the content of the aqueous solvent contained in the aqueous composition according to the present invention is preferably greater than or equal to 60 mass % and more preferably greater than or equal to 70 mass %, with respect to the total mass of the aqueous composition.

The pH of the aqueous composition according to the present invention is preferably higher than 5.5. It is possible to sufficiently dissolve pemetrexed or a salt thereof in the aqueous composition by making the pH of the aqueous composition be higher than 5.5.

In addition, the pH of the aqueous composition according to the present invention is preferably 6.0 to 9.0 and more preferably 6.3 to 8.5, from the viewpoint of preservation stability.

In the present specification, the pH is measured by making the temperature of the aqueous composition be 25° C.

The measurement of the pH can be performed using, for example, a pH meter (device No: F-73, manufactured by Horiba, Ltd., pH electrode: Micro ToupH electrode 9618-10D).

It is preferable that the aqueous composition according to the present invention further contains a pH modifier.

The pH modifier is not particularly limited as long as the pH modifier can be pharmaceutically acceptable and can maintain the pH of the aqueous composition be higher than 5.5.

Specifically, it is preferable that the pH modifier is at least one selected from the group consisting of hydrochloric acid, sodium hydroxide, potassium hydroxide, magnesium hydroxide, calcium hydroxide, phosphoric acid or a salt thereof, citric acid or a salt thereof, tartaric acid or a salt thereof, acetic acid or a salt, succinic acid or a salt thereof, lactic acid or a salt thereof, gluconic acid or a salt thereof, adipic acid or a salt thereof, fumaric acid or a salt thereof, boric acid or a salt thereof, maleic acid or a salt thereof, methanesulfonic acid or a salt thereof, malic acid or a salt thereof, triethanolamine, monoethanolamine, diisopropanolamine, triisopropanolamine, trometamol (tris hydroxymethyl aminomethane), glycine, meglumine, and disodium edetate, and it is more preferable that the pH modifier is at least one selected from the group consisting of hydrochloric acid, sodium hydroxide, phosphoric acid or a salt thereof, citric acid or a salt thereof, triethanolamine, trometamol (tris hydroxymethyl aminomethane), and disodium edetate.

The phosphate or the citrate may be a pharmaceutically acceptable salt, and examples thereof include a salt of alkali metal and phosphoric acid or citric acid, a salt of alkali earth metal and phosphoric acid or citric acid, a salt of transition metal and phosphoric acid or citric acid, and a salt of basic ammonium and phosphoric acid or citric acid.

Specific examples thereof include an alkali metal salt with sodium, potassium, or the like; an alkaline earth metal salt with calcium, magnesium, or the like; a transition metal salt with zinc, iron, cobalt, copper, or the like; and a basic ammonium salt with ammonium, triethanolamine, L-histidine, L-arginine, L-lysine, or the like.

Among these, as the phosphate or the citrate, disodium hydrogen phosphate, sodium dihydrogen phosphate, potassium dihydrogen phosphate, trisodium citrate, disodium citrate, sodium dihydrogen citrate, or the like is preferable, and trisodium citrate or disodium citrate is more preferable.

Any pH modifier may be used alone, or two or more kinds thereof may be used in combination.

The content of the pH modifier in an aqueous composition is not particularly limited, and may be appropriately set in accordance with the type of the pH modifier or the like.

The aqueous composition according to the present invention preferably contains at least one selected from the group consisting of citric acid or a salt thereof as the pH modifier. Accordingly, it is possible to prepare an injection preparation which can suppress generation of insoluble impurities which can be generated during preservation.

The aqueous composition according to the present invention can contain other components, which are pharmaceutically acceptable, as necessary in addition to the pemetrexed or a salt thereof, the specific antioxidant agent, the aqueous solvent, and the pH modifier.

Examples of other components include a stabilizing agent, a solubilizing agent, a tonicity agent, a surfactant, a long-lasting agent, an anti-foaming agent, a colorant, an emulsifying agent, a dispersing agent, a preservative, a preserving agent, a solubilizer, and a solvent, but are not limited thereto.

Examples of the tonicity agent contained in the aqueous composition according to the present invention include monosaccharides such as glucose and fructose; sugars such as sucrose, lactose, cellobiose, raffinose, dextran, chondroitin sulfate, hyaluronic acid, and cyclodextrin; sugar alcohols such as sorbitol, mannitol, and xylitol; inorganic salts such as sodium chloride, potassium chloride, calcium chloride, magnesium chloride, calcium bromide, sodium bromide, sodium pyrophosphate, sodium hydrogen sulfite, sodium bicarbonate, boric acid, and borax; and amines such as taurine, nicotinic acid amide, and benzalkonium chloride, but are not limited thereto.

In the injection preparation of the present invention, the concentration of dissolved oxygen in the aqueous composition is preferably less than or equal to 9 ppm.

By making the concentration of dissolved oxygen in the aqueous composition containing a specific amount of a specific antioxidant agent be less than or equal to 9 ppm, it is possible to improve preservation stability of pemetrexed or a salt thereof contained in the aqueous composition, which is preferable.

The concentration of dissolved oxygen in the aqueous composition is more preferably less than or equal to 7 ppm, still more preferably less than or equal to 3 ppm, still more preferably less than or equal to 0.5 ppm, and still more preferably less than or equal to 0.1 ppm.

In the present specification, the measurement of the concentration of dissolved oxygen in an aqueous composition is not particularly limited, and it is possible to use a method, which is generally used, as a measurement method of the concentration of dissolved oxygen in a solution. For example, it is possible to measure the concentration of dissolved oxygen in an aqueous composition using an oxygen concentration determination device (product name: InLab (registered trademark) ScienceProISM (manufactured by Mettler-Toledo International Inc.)) or a residual oxygen meter (product name: Pack Master manufactured by lijima Electronics Corporation).

Specific examples of the method for measuring the concentration of dissolved oxygen in an aqueous composition include a method for measuring the concentration of dissolved oxygen by bringing an electrode of the oxygen concentration determination device into contact with the aqueous composition. Alternately, another example thereof includes a method for measuring the concentration of dissolved oxygen in an aqueous composition by sticking a sampler needle portion of the oxygen concentration determination device into a container included in an injection preparation and suctioning the aqueous composition in the injection preparation.

In addition, in a case of measuring the concentration of dissolved oxygen in an aqueous composition in an injection preparation which has been preserved for one or more days, it is considered that oxygen dissolved in the aqueous composition and oxygen existing in gas within the container reach equilibrium. Therefore, it is possible to calculate the concentration of oxygen in the aqueous composition by, for example, measuring the concentration of oxygen in gas within the container from Henry's law.

The injection preparation includes a container which encloses an aqueous composition. The air within the container is preferably substituted with inert gas and more preferably substituted with nitrogen gas.

Accordingly, it becomes easy to adjust the concentration of oxygen in the sealed container which encloses the aqueous composition.

In the injection preparation of the present invention, the concentration of oxygen in gas within the container is less than or equal to 0.2 volume %.

By making the concentration of oxygen of the injection preparation containing the aqueous composition containing a specific amount of a specific antioxidant agent be less than or equal to 0.2 volume %, it is possible to significantly improve preservation stability of pemetrexed or a salt thereof contained in the aqueous composition.

The concentration of oxygen in gas within the container is more preferably less than or equal to 0.1 volume % and still more preferably less than 0.05 volume %.

In the concentration of oxygen in gas within the container included in the injection preparation of the present invention, either of measurement of the concentration of oxygen in gas enclosed in the container during the production of the injection preparation, measurement of the concentration of oxygen in gas within the container immediately after the production of the injection preparation, or measurement of the concentration of oxygen in gas within the container after preserving the injection preparation for a certain period of time is included.

In the present specification, the measurement of the concentration of oxygen in gas within the container is not particularly limited, and a method which is generally used can be used as the method for measuring the concentration of oxygen in gas. For example, an oxygen monitor OXY-1 (manufactured by Jikco Ltd.) (measurement method: diaphragm-type galvanic cell type) or a residual oxygen meter Pack Master (manufactured by Iijima Electronics Corporation) (measurement method: diaphragm-type galvanic cell type).

Specific examples of the method for measuring the concentration of oxygen in gas within the container include a method for measuring the concentration of oxygen in gas by reading a display value on a sensor-incorporated oxygen monitor in a glove box when producing an injection preparation while controlling the amount of nitrogen and oxygen which have been injected, so as to have a target oxygen concentration in the glove box (0.1% of minimum resolution). Alternately, another example thereof include a method for measuring the concentration of oxygen in gas by sticking a sampler needle portion of the oxygen concentration determination device into a container included in an injection preparation and suctioning gas in the injection preparation (0.01% of minimum resolution). In the case of the latter method, it is preferable to measure the concentration thereof under a nitrogen atmosphere in order to avoid oxygen outside the container from being mixed in during the measurement.

Examples of the container which encloses an aqueous composition include a vial bottle, an ampule, and a syringe. Among these, a vial bottle is preferable from the viewpoint of handling properties in a medical site.

In addition, a container in which the amount of silicon eluted into water in a case where the container is filled with water and heat treatment is performed for 60 minutes at 121° C. is less than or equal to 1.0 ppm is preferable as the container and a container in which the amount of silicon eluted into water in a case where the container is filled with water and heat treatment is performed for 60 minutes at 121° C. is less than or equal to 0.5 ppm is more preferable as the container.

It is possible to use a commercially available product as the container, and it is possible to use, for example, Resin CZ manufactured by Daikyo Seiko. Ltd., 3010, 3010 Silicort, FY-5, FY-5 Silicort, FY-5 Sulfur Treatment, CS-20 Silicort, CS-30 Silicort, and CS-40 Silicort which are manufactured by Fuji Glass Co., Ltd., 23×43 LA, 23×43 VIST which are manufactured by Daiwa Special Glass Co., Ltd., or the like.

In addition, it is possible to improve preservation stability of pemetrexed or a salt thereof contained in the aqueous composition using a film with oxygen barrier properties, as a package of the container which encloses the aqueous composition.

As the material of the film, alumina-coated polyethylene terephthalate (PET), silica-coated PET, nanocomposite-coated PET, PET, polyvinyl alcohol, an ethylene-vinyl alcohol copolymer, polyvinyl chloride, polyvinylidene chloride, a vinylidene chloride-methyl acrylate copolymer, taxylyleneadipamide, 6 nylon, biaxially stretched nylon, non-stretched nylon, biaxially stretched polypropylene, high density polyethylene, non-stretched polypropylene, polycarbonate, polystyrene, low density polyethylene, or the like can be used.

The oxygen gas permeability of the film is preferably less than or equal to 100 $cm^3/m^2 \cdot 24$ h·atm, more preferably less than or equal to 10 $cm^3/m^2 \cdot 24$ h·atm, and still more preferably less than or equal to 2 $cm^3/m^2 \cdot 24$ h·atm, from the viewpoint of preservation stability.

The container may be single packaged using a film with oxygen barrier properties, or may be packaged using a plurality of films, that is, double or more films, with oxygen barrier properties.

It is possible to fill either space between the container and the outermost package which packages the container, with a deoxidizing agent. Accordingly, it is possible to improve preservation stability of pemetrexed or a salt thereof contained in the aqueous composition.

As the deoxidizing agent, it is possible to use an iron-based self-reactive deoxidizing agent (manufactured by Mitsubishi Gas Chemical Company, Inc., Ageless ZP, Ageless ZJ-PT, Ageless ZJ-PK, Ageless S), an iron-based moisture-dependent deoxidizing agent (manufactured by Mitsubishi Gas Chemical Company, Inc., Ageless FX), a nonferrous self-reactive deoxidizing agent (manufactured by Mitsubishi Gas Chemical Company, Inc., Ageless GLS, Ageless GL-M, Ageless GT), or the like.

In the injection preparation of the present invention, the ratio (number of oxygen molecules/number of pemetrexed molecules) of the number of oxygen molecules with respect to the number of pemetrexed molecules in the injection preparation is less than or equal to 0.0025, more preferably less than or equal to 0.0016, and still more preferably less than or equal to 0.00080, from the viewpoint of significantly suppressing decomposition of pemetrexed or a salt thereof and coloration of the injection preparation during preservation.

Here, when an aqueous composition is enclosed in a container, the ratio (number of oxygen molecules/number of pemetrexed molecules) of the number of oxygen molecules with respect to the number of pemetrexed molecules in the injection preparation is calculated based on a sum of the numbers of oxygen molecules which have been calculated by multiplying the concentration of oxygen in gas within the container and the volume thereof and multiplying the concentration of dissolved oxygen in the aqueous composition and the volume thereof. In addition, when no aqueous composition is enclosed in a container or when an aqueous composition is enclosed in a container and there is no gas (for example, prefilled syringe), the ratio (number of oxygen molecules/number of pemetrexed molecules) of the number of oxygen molecules with respect to the number of pemetrexed molecules in the injection preparation is calculated based on the concentration of dissolved oxygen in the aqueous composition.

In the ratio of the number of oxygen molecules with respect to the number of pemetrexed molecules in the injection preparation in the present invention, either of measurement and calculation of the ratio thereof during the production of the injection preparation, measurement and calculation of the ratio thereof immediately after the production of the injection preparation, or measurement and calculation of the ratio thereof after preserving the injection preparation for a certain period of time is included.

In the present specification, the number of pemetrexed molecules in the injection preparation and the number of oxygen molecules in the injection preparation are respectively calculated in accordance with the following methods.

Number (mol) of pemetrexed molecules=concentration (mol/L) of pemetrexed in aqueous composition×volume (L) of aqueous composition     Equation 1.

Number (mol) of oxygen molecules in injection preparation=number (mol) of oxygen molecules in gas within container+number (mol) of oxygen molecules in aqueous composition     Equation 2.

Number (mol) of oxygen molecules in gas within container=concentration (volume %) of oxygen in gas within container÷100×volume (L) of gas within container÷(0.082×(273.15+temperature (° C.))     Equation 3.

Number (mol) of oxygen molecules in aqueous composition=concentration (mg/L) of dissolved oxygen in aqueous composition÷32÷1000×volume (L) of aqueous composition     Equation 4.

When the measurement method is a method in which an injection preparation is prepared while suppressing the amounts of nitrogen and oxygen, which have been injected, so as to have a target oxygen concentration in the glove box, the temperature in Equation 3 refers to temperature when the aqueous composition is sealed, in a case where a display value of a sensor-incorporated oxygen monitor in a glove box is read. In contrast, in a case where the measurement method is a method in which the concentration of oxygen in gas is measured by sticking a sampler needle portion of an oxygen concentration determination device into an injection preparation and suctioning the gas in the injection preparation, the temperature in Equation 3 refers to temperature during the measurement.

The method for preparing an injection preparation of the present invention is not particularly limited, and any well known method can be used. For example, it is possible to prepare an injection preparation in accordance with the method disclosed in JP2003-521518A.

The method for producing an injection preparation of the present invention includes: producing an aqueous composition which contains (i) pemetrexed or a salt thereof, (ii) at least one antioxidant agent which is selected from the group consisting of ascorbic acid, an ascorbic acid derivative, and salts thereof, and the content of which is 0.0001 mass % to 0.5 mass % with respect to the total mass of the aqueous composition in terms of ascorbic acid, and (iii) an aqueous solvent of greater than or equal to 50 mass % with respect to the total mass of the aqueous composition; and filling the container with the aqueous composition under an inert gas atmosphere or substituting gas within a container with inert gas after filling the container with the aqueous composition.

Regarding the aqueous composition and the container, it is possible to apply the description in the above-described section of the aqueous composition thereto as it is.

Nitrogen is preferable as inert gas.

The method for substituting gas within a container with inert gas after filling the container with the aqueous composition is not particularly limited. For example, it is possible to use a glove box, a capping machine or a vacuum capping machine which has a function of capping under an inert gas stream, or a chamber which has a function of capping in a sealed state.

Specific examples of the method for substituting gas within a container with inert gas include substituting gas within a container with inert gas by tightly plugging a vial in a glove box using a rubber plug after the vial, which is filled with an aqueous composition, and the rubber plug are placed in the glove box and inert gas is blown so as to have a target oxygen concentration in the glove box. Alternately, it is possible to substitute gas within a container with inert gas by repeating evacuating and blowing of inert gas after blocking the vial filled with an aqueous composition from outside air by covering the vial with a chamber component. Alternately, it is possible to substitute gas within a container with inert gas by tightly plugging a vial, which is filled with an aqueous composition and is half-capped, in a chamber which has a function of capping in a sealed state after installing the vial in the chamber and blowing inert gas into the chamber so as to have a target oxygen concentration.

<Second Aqueous Composition>

A second aqueous composition according to the present invention contains (i) pemetrexed or a salt thereof, (ii) at least one antioxidant agent A which is selected from the group consisting of ascorbic acid, an ascorbic acid derivative, and salts thereof, and the content of which is 0.001 mass % to 1.0 mass % with respect to the total mass of the second aqueous composition in terms of ascorbic acid, (iii) at least one antioxidant agent B which is selected from the group consisting of a compound having a thiol group or a salt thereof, and a compound having a sulfide bond or a salt thereof, and the content of which is 0.00050 mass % to 0.15 mass % with respect to the total mass of the second aqueous composition, and (iv) an aqueous solvent of greater than or equal to 50 mass % with respect to the total mass of the second aqueous composition.

In addition, the second aqueous composition may contain other components as necessary.

Regarding pemetrexed or a salt thereof, an aqueous solvent, pharmaceutically acceptable other components, a container, a package of the container, and the like, it is possible to apply the description in the above-described section of the aqueous composition thereto as it is.

In the second aqueous composition according to the present invention, it is possible to suppress coloration of the second aqueous composition by combining a specific amount of the antioxidant agent B with the antioxidant agent A and making the concentration of oxygen in gas within the container which encloses the second aqueous composition be less than or equal to 1.5 volume %.

(Antioxidant Agent A)

The second aqueous composition of the present invention contains at least one antioxidant agent A which is selected from the group consisting of ascorbic acid, an ascorbic acid derivative, and salts thereof, and the content of which is 0.001 mass % to 1.0 mass % with respect to the total mass of the second aqueous composition in terms of ascorbic acid.

Regarding ascorbic acid, an ascorbic acid derivative, and the types of salts thereof, it is possible to apply the description in the above-described section of the aqueous composition thereto as it is.

In addition, the antioxidant agent A may be used in combination with other antioxidant agents.

As other antioxidant agents, it is possible to apply the description in the above-described section of the aqueous composition thereto as it is.

The content of the antioxidant agent A contained in the second aqueous composition according to the present invention is 0.001 mass % to 1.0 mass % with respect to the total mass of the second aqueous composition in terms of ascorbic acid.

In both cases where the content of the antioxidant agent A is made to be smaller than 0.001 mass % with respect to the total mass of the second aqueous composition in terms of ascorbic acid or where the content of the antioxidant agent A is made to be larger than 1.0 mass % with respect to the total mass of the second aqueous composition in terms of ascorbic acid, preservation stability of pemetrexed or a salt thereof deteriorates, which is not preferable.

In addition, in order to further improve the preservation stability, the content of the antioxidant agent A contained in the second aqueous composition according to the present invention is more preferably 0.005 mass % to 0.5 mass % and still more preferably 0.005 mass % to 0.1 mass %, with respect to the total mass of the second aqueous composition in terms of ascorbic acid.

Here, as is described in the above-described section of the aqueous composition, the expression "in terms of ascorbic acid" means that the content of the specific antioxidant agent is calculated by employing the mass of the ascorbic acid itself with respect to the ascorbic acid and by employing the mass of a partial structure derived from ascorbic acid contained in an derivative or a salt with respect to an ascorbic acid derivative, a salt of ascorbic acid, and a salt of the ascorbic acid derivative.

(Antioxidant Agent B)

The second aqueous composition in the present invention contains at least one antioxidant agent B which is selected from the group consisting of a compound having a thiol group or a salt thereof, and a compound having a sulfide bond or a salt thereof, and the content of which is 0.00050 mass % to 0.15 mass % with respect to the total mass of the second aqueous composition.

The second aqueous composition of the present invention may contain at least one selected from the group consisting of a compound having a thiol group or a salt thereof, and a compound having a sulfide bond or a salt thereof, and has an action of reducing active oxygen species which becomes a cause of oxidative decomposition of pemetrexed or a salt thereof. Therefore, it is preferable that the second aqueous composition of the present invention contains a compound having a thiol group or a salt thereof.

Examples of the compound having a thiol group or a salt thereof include thioglycerol, cysteine or a salt thereof, and thioglycolic acid or a salt thereof, thiomalic acid or a salt thereof, glutathione, a polypeptide containing cysteine residues, methyl mercaptan, aminoethyl thiol, N-acetyl-L-cysteine, 2-mercapto-ethanol, and dithioerythritol.

As the salts of cysteine, thioglycolic acid, and thiomalic acid, any pharmaceutically acceptable salts may be used. Examples thereof include a salt of alkali metal and cysteine, thioglycolic acid, and thiomalic acid, a salt of alkali earth metal and cysteine, thioglycolic acid, and thiomalic acid, a salt of transition metal and cysteine, thioglycolic acid, and thiomalic acid, and a salt of basic ammonium and cysteine, thioglycolic acid, and thiomalic acid.

Specific examples thereof include an alkali metal salt with sodium, potassium, or the like; an alkaline earth metal salt with calcium, magnesium, or the like; a transition metal salt with zinc, iron, cobalt, copper, or the like; a basic ammonium salt with ammonium, triethanolamine, L-histidine, L-arginine, L-lysine, or the like, hydrochloride, formate, acetate, maleate, fumarate, and tartrate.

Among these, examples of the salt of cysteine include cysteine hydrochloride, examples of the salt of thioglycolic acid include sodium thioglycolate, and potassium thioglycolate, and examples of the salt of thiomalic acid include sodium thiomalate and potassium thiomalate.

As the compound having a thiol group or a salt thereof, cysteine or a salt thereof is preferably included and cysteine or a salt thereof and thioglycerol is more preferably included from the viewpoint of suppression of decomposition of pemetrexed or a salt thereof.

Examples of the compound having a sulfide bond or a salt thereof include DL-methionine, L-methionine, mercapturic acid, biotin, diallyl sulfide, thiodisuccinic acid, 2-[(carboxymethyl)thio]butandioic acid, thiodipropionic acid, probucol, dilauryl thiodipropionic acid ester, carbamic acid-3-phenothiazinyl ester, 4,4'-thiobis(6-tert-butyl-m-cresol), dimethyl disulfide, cystine, and DL-lipoic acid.

Among these, as the compound having a sulfide bond or a salt thereof, DL-methionine, L-methionine, and biotin are preferable.

Any antioxidant agent B may be used alone, or two or more kinds thereof may be used in combination.

The content of the antioxidant agent B contained in the second aqueous composition according to the present invention is 0.00050 mass % to 0.15 mass % with respect to the total mass of the second aqueous composition.

It is possible to improve preservation stability of pemetrexed or a salt thereof by making the content of the antioxidant agent B be greater than or equal to 0.00050 mass % with respect to the total mass of the second aqueous composition. In addition, it is preferable to make the content of the antioxidant agent B be less than or equal to 0.15 mass % in terms of ease of application of the antioxidant agent B to a human body.

In addition, in order to improve the preservation stability of pemetrexed or a salt thereof, the content of the antioxidant agent B contained in the second aqueous composition according to the present invention is more preferably 0.0050 mass % to 0.15 mass %, still more preferably 0.010 mass % to 0.15 mass %, and still more preferably 0.020 mass % to 0.13 mass %, with respect to the total mass of the second aqueous composition.

The ratio of the content of the antioxidant agent B to the content of the antioxidant agent A (antioxidant agent A: antioxidant agent B) is preferably 1:0.05 to 1:13 on a mass basis. Accordingly, it is possible to exhibit at least one effect of an effect of suppressing coloration of the aqueous composition and an effect of suppressing decomposition of pemetrexed or a salt thereof.

In addition, ratio of the content of the antioxidant agent B to the content of the antioxidant agent A (antioxidant agent A: antioxidant agent B) is more preferably 1:0.2 to 1:5 and still more preferably 1:0.2 to 1:6 on a mass basis.

The content ratio (pemetrexed or a salt thereof: (total amount of antioxidant agent A and antioxidant agent B)) of the total amount of antioxidant agent A and antioxidant agent B to pemetrexed or a salt thereof in the second aqueous composition is preferably 2.2:1 to 2500:1, more preferably 10:1 to 250:1, and still more preferably 20:1 to 250:1, from the viewpoint of preservation stability of pemetrexed or a salt thereof on a mass basis.

The pH of the second aqueous composition is preferably higher than 5.5 and lower than or equal to 9.5. By making the pH of the second aqueous composition be within this range, it is possible to homogeneously dissolve pemetrexed or a salt thereof, which is preferable.

In addition, the pH of the second aqueous composition is more preferably 6.0 to 9.0, still more preferably 6.5 to 8.0, and still more preferably 7.0 to 8.0, from the viewpoint of preventing of coloration of an injection preparation and suppressing of decomposition of pemetrexed or a salt thereof.

In the second aqueous composition, it is most preferable that the pH is 7.0 to 8.0, the content of the antioxidant agent A is 0.005 mass % to 0.1 mass %, the content of antioxidant agent B is 0.05 mass % to 0.13 mass %, the antioxidant agent A is ascorbic acid, and the antioxidant agent B is cysteine hydrochloride and thioglycerol.

It is preferable that the second aqueous composition according to the present invention further contains a pH modifier.

The pH modifier is not particularly limited as long as the pH modifier is pharmaceutically acceptable and can maintain the pH of the second aqueous composition to be higher than 5.5 and lower than or equal to 9.5. Specific examples of the pH modifier include the components described in the above-described section of the aqueous composition.

Among these, it is preferable that the pH modifier contained in the second aqueous composition is at least one selected from the group consisting of hydrochloric acid, sodium hydroxide, phosphoric acid or a salt thereof, citric acid or a salt thereof, triethanolamine, trometamol (tris hydroxymethyl aminomethane), and disodium edetate.

The phosphate or the citrate may be a pharmaceutically acceptable salt, and examples thereof include a salt of alkali metal and phosphoric acid or citric acid, a salt of alkali earth metal and phosphoric acid or citric acid, a salt of transition metal and phosphoric acid or citric acid, and a salt of basic ammonium and phosphoric acid or citric acid.

Specific examples thereof include an alkali metal salt with sodium, potassium, or the like; an alkaline earth metal salt with calcium, magnesium, or the like; a transition metal salt with zinc, iron, cobalt, copper, or the like; and a basic ammonium salt with ammonium, triethanolamine, L-histidine, L-arginine, L-lysine, or the like.

Among these, as the phosphate or the citrate, disodium hydrogen phosphate, sodium dihydrogen phosphate, potassium dihydrogen phosphate, trisodium citrate, disodium citrate, sodium dihydrogen citrate, or the like is preferable, and trisodium citrate or disodium citrate is more preferable.

It is more preferable that at least one selected from the group consisting of citrate or a salt thereof is included as the pH modifier contained in the second aqueous composition according to the present invention. Accordingly, it is possible to prepare an injection preparation which can suppress generation of insoluble impurities which can be generated during preservation.

Any pH modifier may be used alone, or two or more kinds thereof may be used in combination.

The content of the pH modifier in the second aqueous composition is not particularly limited, and may be appropriately set in accordance with the type of the pH modifier or the like.

In the second injection preparation of the present invention, the concentration of dissolved oxygen in the second aqueous composition is preferably less than or equal to 9 ppm.

By making the concentration of dissolved oxygen in the second aqueous composition containing a specific amount of an antioxidant agent A and a specific amount of an antioxidant agent B be less than or equal to 9 ppm, it is possible to improve preservation stability of pemetrexed or a salt thereof contained in the second aqueous composition, which is preferable.

The concentration of dissolved oxygen in the second aqueous composition is more preferably less than or equal to 7 ppm, still more preferably less than or equal to 3 ppm, still more preferably less than or equal to 0.5 ppm, and still more preferably less than or equal to 0.1 ppm.

The second injection preparation includes a container which encloses a second aqueous composition. The air within the container is preferably substituted with inert gas and more preferably substituted with nitrogen gas.

Accordingly, it becomes easy to adjust the concentration of oxygen in the sealed container which encloses the second aqueous composition.

In the second injection preparation of the present invention, the concentration of oxygen in gas within the container is less than or equal to 1.5 volume %. By making the concentration of oxygen of the second injection preparation containing the second aqueous composition containing a specific amount of an antioxidant agent A and a specific amount of an antioxidant agent B be less than or equal to 1.5 volume %, it is possible to significantly improve the suppression of decomposition of pemetrexed or a salt thereof contained in the second aqueous composition and to suppress coloration of the second aqueous composition.

Even if the concentration of oxygen in gas within the container is within the oxygen concentration range of less than or equal to 1.5 volume %, the effect which can be exhibited by the second injection preparation of the present invention is not impaired.

The concentration of oxygen in gas within the container is preferably less than or equal to 1.0 volume % and more preferably less than or equal to 0.6 volume %.

In the concentration of oxygen in gas within the container included in the second injection preparation of the present invention, either of measurement of the concentration of oxygen in gas enclosed in the container during the production of the injection preparation, measurement of the concentration of oxygen in gas within the container immediately after the production of the injection preparation, or measurement of the concentration of oxygen in gas within the container after preserving the injection preparation for a certain period of time is included.

In the second injection preparation of the present invention, the ratio (number of oxygen molecules/number of pemetrexed molecules) of the number of oxygen molecules with respect to the number of pemetrexed molecules in the injection preparation is less than or equal to 0.0120, more preferably less than or equal to 0.0080, and still more preferably less than or equal to 0.0048, from the viewpoint of significantly suppressing decomposition of pemetrexed or a salt thereof and coloration of the injection preparation during preservation.

The ratio of the number of oxygen molecules with respect to the number of pemetrexed molecules in the injection preparation in the second injection preparation of the present invention can be measured and calculated through the above-described method.

In the ratio of the number of oxygen molecules with respect to the number of pemetrexed molecules in the injection preparation, in the second injection preparation of the present invention, either of measurement and calculation of the ratio thereof during the production of the injection preparation, measurement and calculation of the ratio thereof immediately after the production of the injection preparation, or measurement and calculation of the ratio thereof after preserving the injection preparation for a certain period of time is included.

The method for preparing a second injection preparation of the present invention is not particularly limited, and any well known method can be used. For example, it is possible to prepare an injection preparation in accordance with the method disclosed in JP2003-521518A.

The method for producing a second injection preparation of the present invention includes: producing a second aqueous composition which contains (i) pemetrexed or a salt thereof, (ii) at least one antioxidant agent A which is selected from the group consisting of ascorbic acid, an ascorbic acid derivative, and salts thereof, and the content of which is 0.001 mass % to 1.0 mass % with respect to the total mass of the second aqueous composition in terms of ascorbic acid, (iii) at least one antioxidant agent B which is selected from the group consisting of a compound having a thiol group or a salt thereof, and a compound having a sulfide bond or a salt thereof, and the content of which is 0.0005 mass % to 0.1 mass % with respect to the total mass of the second aqueous composition, and (iv) an aqueous solvent of greater than or equal to 50 mass % with respect to the total mass of the second aqueous composition; and filling the container with the second aqueous composition under an inert gas atmosphere or substituting gas within a container with inert gas after filling the container with the second aqueous composition.

Regarding the second aqueous composition and the container, it is possible to apply the description in the above-described section of the second aqueous composition thereto as it is.

Nitrogen is preferable as inert gas.

The method for substituting gas within a container with inert gas after filling the container with the aqueous composition is not particularly limited. For example, it is possible to use a glove box, a capping machine or a vacuum capping machine which has a function of capping under an inert gas stream, or a chamber which has a function of capping in a sealed state.

Specific examples of the method for substituting gas within a container with inert gas include substituting gas within a container with inert gas by tightly plugging a vial in a glove box using a rubber plug after the vial, which is filled with an aqueous composition, and the rubber plug are placed in the glove box and inert gas is blown so as to have a target oxygen concentration in the glove box. Alternately, it is possible to substitute gas within a container with inert gas by repeating evacuating and blowing of inert gas after blocking the vial filled with an aqueous composition from outside air by covering the vial with a chamber component. Alternately, it is possible to substitute gas within a container with inert gas by tightly plugging a vial, which is filled with an aqueous composition and is half-capped, in a chamber which has a function of capping in a sealed state after installing the vial in the chamber and blowing inert gas into the chamber so as to have a target oxygen concentration.

EXAMPLES

Hereinafter, Examples of the present invention will be described in more detail. However, the present invention is not limited to the following Examples as long as Examples do not depart from the gist of the present invention.

Example 1: Preparation of Injection Preparation (C-1)

21.0 g of injection water (manufactured by Hikari Pharmaceutical Co., Ltd.), 230 mg of a 1 mass % aqueous solution of ascorbic acid (manufactured by DSM Nutrition Japan) which had been prepared in advance, and pemetrexed disodium (575 mg as pemetrexed) were weighed into a clean 50 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residue was not recognized while performing external observation with the naked eye.

1 N (1 mol/L) hydrochloric acid (manufactured by Wako Pure Chemical Industries, Ltd.) was added to the prepared solution little by little and the pH value was adjusted to 7.0. Injection water was added thereto such that the total amount of the solution became 23.0 g.

The prepared solution was placed in a glove box, and nitrogen substitution in the solution was performed (at a concentration of dissolved oxygen of 0.01 ppm) by stirring the solution for 2 hours at room temperature. Thereafter, the solution was sterilized and filtered using a 0.2 μm filter (made of PTFE) under nitrogen atmosphere (lower than or equal to 0.1 v/v % of oxygen concentration). Then, a vial (manufactured by Fuji Glass Co., Ltd., vial bottle 3010 Silicort) was filled with 2 mL of the sterilized and filtered solution. A target injection preparation (C-1, 2.50 mass % of concentration of pemetrexed, 0.01 mass % of concentration of ascorbic acid) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., aluminum seal B (middle)) so as to cover the vial and the mouth of the rubber plug, and clamping the aluminum seal using a clipper from the above. It was confirmed that the concentration of dissolved oxygen being 0.01 ppm and the concentration of oxygen (less than 0.1 v/v %) of a container space did not change even in a sample during the preservation.

Example 2: Preparation of Injection Preparation (C-2)

18.0 g of injection water (manufactured by Hikari Pharmaceutical Co., Ltd.), 230 mg of a 1 mass % aqueous solution of ascorbic acid (manufactured by DSM Nutrition Japan) which had been prepared in advance, 23.0 mg of citric acid (manufactured by Merck, citric acid monohydrate), 300 mg of 1 N sodium hydroxide (manufactured by Wako Pure Chemical Industries, Ltd.), and pemetrexed disodium (575 mg as pemetrexed) were weighed into a clean 50 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residue was not recognized while performing external observation with the naked eye.

1 N (1 mol/L) sodium hydroxide (manufactured by Wako Pure Chemical Industries, Ltd.) was added to the prepared solution little by little and the pH value was adjusted to 6.5. Injection water was added thereto such that the total amount of the solution became 23.0 g.

The prepared solution was placed in a glove box, and nitrogen substitution in the solution was performed (at a concentration of dissolved oxygen of 0.01 ppm) by stirring the solution for 2 hours at room temperature. Thereafter, the solution was sterilized and filtered using a 0.2 μm filter (made of PTFE) under nitrogen atmosphere (lower than or equal to 0.1 v/v % of oxygen concentration). Then, a vial (manufactured by Fuji Glass Co., Ltd., vial bottle 3010 Silicort) was filled with 2 mL of the sterilized and filtered solution. A target injection preparation (C-2, 2.50 mass % of concentration of pemetrexed, 0.01 mass % of concentration of ascorbic acid) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., aluminum seal B (middle)) so as to cover the vial and the mouth of the rubber plug, and clamping the aluminum seal using a clipper from the above. It was confirmed that the concentration of dissolved oxygen being 0.01 ppm and the concentration of oxygen (less than 0.1 v/v %) of a container space did not change even in a sample during the preservation.

Example 3: Preparation of Injection Preparation (C-3)

A target injection preparation (C-3, 2.50 mass % of concentration of pemetrexed, 0.01 mass % of concentration of ascorbic acid) was obtained similarly to Example 2 except that the amount of citric acid described in Example 2 was changed to 230 mg and the amount of 1N sodium hydroxide was changed to 3.00 g. It was confirmed that the concentration of dissolved oxygen being 0.01 ppm and the concentration of oxygen (less than 0.1 v/v %) of a container space did not change even in a sample during the preservation.

Example 4: Preparation of Injection Preparation (C-4)

4.10 g of injection water (manufactured by Hikari Pharmaceutical Co., Ltd.), 45.0 mg of a 1 mass % aqueous solution of ascorbic acid (manufactured by BASF) which had been prepared in advance, 23.0 mg of disodium hydrogen phosphate (Wako Pure Chemical Industries, Ltd., "exclusive for production" of sodium hydrogen phosphate hydrate), and pemetrexed disodium (113 mg as pemetrexed) were weighed into a clean 10 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residue was not recognized while performing external observation with the naked eye.

1 N hydrochloric acid (manufactured by Wako Pure Chemical Industries, Ltd.) was added to the prepared solution little by little and the pH value was adjusted to 7.0. Injection water was added thereto such that the total amount of the solution became 4.50 g.

The prepared solution was placed in a glove box, and nitrogen substitution in the solution was performed (at a concentration of dissolved oxygen of 0.01 ppm) by stirring the solution for 2 hours at room temperature. Thereafter, the solution was sterilized and filtered using a 0.2 μm filter (made of PTFE) under nitrogen atmosphere (lower than or equal to 0.1 v/v % of oxygen concentration). Then, a vial (manufactured by Fuji Glass Co., Ltd., vial bottle 3010 Silicort) was filled with 1 mL of the sterilized and filtered solution. A target injection preparation (C-4, 2.50 mass % of concentration of pemetrexed, 0.01 mass % of concentration of ascorbic acid) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., aluminum seal B (middle)) so as to cover the vial and the mouth of the rubber plug, and clamping the aluminum seal using a clipper from the above. It was confirmed that the concentration of dissolved oxygen being 0.01 ppm and the concentration of oxygen (less than 0.1 v/v %) of a container space did not change even in a sample during the preservation.

Example 5: Preparation of Injection Preparation (C-5)

9.00 g of injection water (manufactured by Hikari Pharmaceutical Co., Ltd.), 100 mg of a 1 mass % solution of ascorbic acid (manufactured by DSM Nutrition Japan) which had been prepared in advance, 100 mg of a 1 mass % aqueous solution of disodium edetate (manufactured by Dojindo Molecular Technologies, Inc., 2NA(EDTA.2Na)) which had been prepared in advance, and pemetrexed disodium trihydrate (250 mg as pemetrexed) were weighed into a clean 50 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residue was not recognized while performing external observation with the naked eye.

1 N hydrochloric acid (manufactured by Wako Pure Chemical Industries, Ltd.) was added to the prepared solution little by little and the pH value was adjusted to 7.0. Injection water was added thereto such that the total amount of the solution became 10.0 g.

The prepared solution was placed in a glove box, and nitrogen substitution in the solution was performed (at a concentration of dissolved oxygen of 0.01 ppm) by stirring the solution for 2 hours at room temperature. Thereafter, the solution was sterilized and filtered using a 0.2 μm filter (made of PTFE) under nitrogen atmosphere (lower than or equal to 0.1 v/v % of oxygen concentration). Then, a vial (manufactured by Fuji Glass Co., Ltd., vial bottle 3010 Silicort) was filled with 1 mL of the sterilized and filtered solution. A target injection preparation (C-5, 2.50 mass % of concentration of pemetrexed, 0.01 mass % of concentration of ascorbic acid) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., aluminum seal B (middle)) so as to cover the vial and the mouth of the rubber plug, and clamping the aluminum seal using a clipper from the above. It was confirmed that the concentration of dissolved oxygen being 0.01 ppm and the concentration of oxygen (less than 0.1 v/v %) of a container space did not change even in a sample during the preservation.

Example 6: Preparation of Injection Preparation (C-6)

4.00 g of injection water (manufactured by Hikari Pharmaceutical Co., Ltd.), 5.0 mg of triethanolamine (manufactured by Wako Pure Chemical Industries, Ltd.), 50.0 mg of a 1 mass % aqueous solution of ascorbic acid (manufactured by DSM Nutrition Japan) which had been prepared in advance, and pemetrexed disodium (125 mg as pemetrexed) were weighed into a clean 15 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residue was not recognized while performing external observation with the naked eye.

1 N hydrochloric acid (manufactured by Wako Pure Chemical Industries, Ltd.) was added to the prepared solution little by little and the pH value was adjusted to 7.0. Injection water was added thereto such that the total amount of the solution became 5.0 g.

The prepared solution was placed in a glove box, and nitrogen substitution in the solution was performed (at a concentration of dissolved oxygen of 0.01 ppm) by stirring the solution for 2 hours at room temperature. Thereafter, the solution was sterilized and filtered using a 0.2 µm filter (made of PTFE) under nitrogen atmosphere (lower than or equal to 0.1 v/v % of oxygen concentration). Then, a vial (manufactured by Fuji Glass Co., Ltd., vial bottle 3010 Silicort) was filled with 1 mL of the sterilized and filtered solution. A target injection preparation (C-6, 2.50 mass % of concentration of pemetrexed, 0.01 mass % of concentration of ascorbic acid) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., aluminum seal B (middle)) so as to cover the vial and the mouth of the rubber plug, and clamping the aluminum seal using a clipper from the above. It was confirmed that the concentration of dissolved oxygen being 0.01 ppm and the concentration of oxygen (less than 0.1 v/v %) of a container space did not change even in a sample during the preservation.

Example 7: Preparation of Injection Preparation (C-7)

1.10 g of injection water (manufactured by Hikari Pharmaceutical Co., Ltd.), 15.0 mg of a 1 mass % aqueous solution of sodium ascorbate (manufactured by Wako Pure Chemical Industries, Ltd.) which had been prepared in advance, 15.0 mg of disodium hydrogen phosphate (Wako Pure Chemical Industries, Ltd., "exclusive for production" of sodium hydrogen phosphate hydrate), and pemetrexed disodium (37.5 mg as pemetrexed) were weighed into a clean 5 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residue was not recognized while performing external observation with the naked eye.

1 N hydrochloric acid (manufactured by Wako Pure Chemical Industries, Ltd.) was added to the prepared solution little by little and the pH value was adjusted to 7.0. Injection water was added thereto such that the total amount of the solution became 1.50 g.

The prepared solution was placed in a glove box, and nitrogen substitution in the solution was performed (at a concentration of dissolved oxygen of 0.01 ppm) by stirring the solution for 2 hours at room temperature. Thereafter, the solution was sterilized and filtered using a 0.2 µm filter (made of PTFE) under nitrogen atmosphere (lower than or equal to 0.1 v/v % of oxygen concentration). Then, a vial (manufactured by Fuji Glass Co., Ltd., vial bottle 3010 Silicort) was filled with 1 mL of the sterilized and filtered solution. A target injection preparation (C-7, 2.50 mass % of concentration of pemetrexed, 0.0089 mass % of concentration of a specific antioxidant agent in terms of ascorbic acid (0.01 mass % of concentration of sodium ascorbate)) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., aluminum seal B (middle)) so as to cover the vial and the mouth of the rubber plug, and clamping the aluminum seal using a clipper from the above. It was confirmed that the concentration of dissolved oxygen being 0.01 ppm and the concentration of oxygen (less than 0.1 v/v %) of a container space did not change even in a sample during the preservation.

Example 8: Preparation of Injection Preparation (C-8)

6.50 g of injection water (manufactured by Hikari Pharmaceutical Co., Ltd.), 70.0 mg of a 1 mass % aqueous solution of ascorbic acid (manufactured by BASF) which had been prepared in advance, 7.0 mg of trisodium citrate (manufactured by Wako Pure Chemical Industries, Ltd.), and pemetrexed disodium trihydrate (175 mg as pemetrexed) were weighed into a clean 15 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residue was not recognized while performing external observation with the naked eye.

1 N hydrochloric acid (manufactured by Wako Pure Chemical Industries, Ltd.) was added to the prepared solution little by little and the pH value was adjusted to 6.1. Injection water was added thereto such that the total amount of the solution became 7.00 g.

The prepared solution was placed in a glove box, and nitrogen substitution in the solution was performed (at a concentration of dissolved oxygen of 0.01 ppm) by stirring the solution for 2 hours at room temperature. Thereafter, the solution was sterilized and filtered using a 0.2 µm filter (made of PTFE) under nitrogen atmosphere (lower than or equal to 0.1 v/v % of oxygen concentration). Then, a vial (manufactured by Fuji Glass Co., Ltd., vial bottle FY-5) was filled with 2 mL of the sterilized and filtered solution. A target injection preparation (C-8, 2.50 mass % of concentration of pemetrexed, 0.01 mass % of concentration of ascorbic acid) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., aluminum seal B (middle)) so as to cover the vial and the mouth of the rubber plug, and clamping the aluminum seal using a clipper from the above. It was confirmed that the concentration of dissolved oxygen being 0.01 ppm and the concentration of oxygen (less than 0.1 v/v %) of a container space did not change even in a sample during the preservation.

Example 9: Preparation of Injection Preparation (C-9)

A target injection preparation (C-9, 2.50 mass % of concentration of pemetrexed, 0.01 mass % of concentration of ascorbic acid) was obtained similarly to Example 8 except that the pH described in Example 8 was changed to 6.6.

It was confirmed that the concentration of dissolved oxygen being 0.01 ppm and the concentration of oxygen (less than 0.1 v/v %) of a container space did not change even in a sample during the preservation.

Example 10: Preparation of Injection Preparation (C-10)

A target injection preparation (C-10, 2.50 mass % of concentration of pemetrexed, 0.01 mass % of concentration of ascorbic acid) was obtained similarly to Example 8 except that the 1 N hydrochloric acid described in Example 8 was changed to 1 N sodium hydroxide (manufactured by Wako Pure Chemical Industries, Ltd.) and the pH value described in Example 8 was changed to 7.5. It was confirmed that the concentration of dissolved oxygen being 0.01 ppm and the concentration of oxygen (less than 0.1 v/v %) of a container space did not change even in a sample during the preservation.

Example 11: Preparation of Injection Preparation (C-11)

A target injection preparation (C-11, 2.50 mass % of concentration of pemetrexed, 0.01 mass % of concentration of ascorbic acid) was obtained similarly to Example 8 except that the 1 N hydrochloric acid described in Example 8 was changed to 1 N sodium hydroxide (manufactured by Wako Pure Chemical Industries, Ltd.) and the pH value described in Example 8 was changed to 8.0. It was confirmed that the concentration of dissolved oxygen being 0.01 ppm and the concentration of oxygen (less than 0.1 v/v %) of a container space did not change even in a sample during the preservation.

Example 12: Preparation of Injection Preparation (C-12)

2.30 g of injection water (manufactured by Hikari Pharmaceutical Co., Ltd.), 25.0 mg of a 1 mass % aqueous solution of ascorbic acid (manufactured by BASF) which had been prepared in advance, 25.0 mg of trisodium citrate (manufactured by Wako Pure Chemical Industries, Ltd.), and pemetrexed disodium (62.5 mg as pemetrexed) were weighed into a clean 5 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residue was not recognized while performing external observation with the naked eye.

0.1 N sodium hydroxide (manufactured by Wako Pure Chemical Industries, Ltd.) was added to the prepared solution little by little and the pH value was adjusted to 9.0. Injection water was added thereto such that the total amount of the solution became 2.50 g.

The prepared solution was placed in a glove box, and nitrogen substitution in the solution was performed (at a concentration of dissolved oxygen of 0.01 ppm) by stirring the solution for 2 hours at room temperature. Thereafter, the solution was sterilized and filtered using a 0.2 μm filter (made of PTFE) under nitrogen atmosphere (lower than or equal to 0.1 v/v % of oxygen concentration). Then, a vial (manufactured by Fuji Glass Co., Ltd., vial bottle 3010 Silicort) was filled with 1 mL of the sterilized and filtered solution. A target injection preparation (C-12, 2.50 mass % of concentration of pemetrexed, 0.01 mass % of concentration of ascorbic acid) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., aluminum seal B (middle)) so as to cover the vial and the mouth of the rubber plug, and clamping the aluminum seal using a clipper from the above. It was confirmed that the concentration of dissolved oxygen being 0.01 ppm and the concentration of oxygen (less than 0.1 v/v %) of a container space did not change even in a sample during the preservation.

Example 13: Preparation of Injection Preparation (C-13)

4.0 g of injection water (manufactured by Hikari Pharmaceutical Co., Ltd.), 5.0 mg of a 1 mass % aqueous solution of ascorbic acid (manufactured by DSM Nutrition Japan) which had been prepared in advance, and pemetrexed disodium (125 mg as pemetrexed) were weighed into a clean 15 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residue was not recognized while performing external observation with the naked eye.

1 N hydrochloric acid (manufactured by Wako Pure Chemical Industries, Ltd.) was added to the prepared solution little by little and the pH value was adjusted to 7.0. Injection water was added thereto such that the total amount of the solution became 5.0 g.

The prepared solution was placed in a glove box, and nitrogen substitution in the solution was performed (at a concentration of dissolved oxygen of 0.01 ppm) by stirring the solution for 2 hours at room temperature. Thereafter, the solution was sterilized and filtered using a 0.2 μm filter (made of PTFE) under nitrogen atmosphere (lower than or equal to 0.1 v/v % of oxygen concentration). Then, a vial (manufactured by Fuji Glass Co., Ltd., vial bottle 3010 Silicort) was filled with 1 mL of the sterilized and filtered solution. A target injection preparation (C-13, 2.50 mass % of concentration of pemetrexed, 0.001 mass % of concentration of ascorbic acid) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., aluminum seal B (middle)) so as to cover the vial and the mouth of the rubber plug, and clamping the aluminum seal using a clipper from the above. It was confirmed that the concentration of dissolved oxygen being 0.01 ppm and the concentration of oxygen (less than 0.1 v/v %) of a container space did not change even in a sample during the preservation.

Example 14: Preparation of Injection Preparation (C-14)

A target injection preparation (C-14, 2.50 mass % of concentration of pemetrexed, 0.0001 mass % of concentration of ascorbic acid) was obtained similarly to Example 13 except that the amount of 1 mass % aqueous solution of ascorbic acid described in Example 13 was changed to 0.5 mg. It was confirmed that the concentration of dissolved oxygen being 0.01 ppm and the concentration of oxygen (less than 0.1 v/v %) of a container space did not change even in a sample during the preservation.

Example 15: Preparation of Injection Preparation (C-15)

6.50 g of injection water (manufactured by Hikari Pharmaceutical Co., Ltd.), 700 mg of a 1 mass % aqueous solution of ascorbic acid (manufactured by BASF) which had been prepared in advance, and pemetrexed disodium trihydrate (175 mg as pemetrexed) were weighed into a clean 15 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residue was not recognized while performing external observation with the naked eye.

1 N sodium hydroxide (manufactured by Wako Pure Chemical Industries, Ltd.) was added to the prepared solution little by little and the pH value was adjusted to 7.0. Injection water was added thereto such that the total amount of the solution became 7.00 g.

The prepared solution was placed in a glove box, and nitrogen substitution in the solution was performed (at a concentration of dissolved oxygen of 0.01 ppm) by stirring the solution for 2 hours at room temperature. Thereafter, the solution was sterilized and filtered using a 0.2 μm filter (made of PTFE) under nitrogen atmosphere (lower than 0.1 v/v % of oxygen concentration). Then, a vial (manufactured by Fuji Glass Co., Ltd., vial bottle FY-5) was filled with 2 mL of the sterilized and filtered solution. A target injection preparation (C-15, 2.50 mass % of concentration of pemetrexed, 0.10 mass % of concentration of ascorbic acid) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., aluminum seal B (middle)) so as to cover the vial and the mouth of the rubber plug, and clamping the aluminum seal using a clipper from the above. It was confirmed that the concentration of dissolved oxygen being 0.01 ppm and the concentration of oxygen (less than 0.1 v/v %) of a container space did not change even in a sample during the preservation.

Example 16: Preparation of Injection Preparation (C-16)

A target injection preparation (C-16, 2.50 mass % of concentration of pemetrexed, 0.30 mass % of concentration of ascorbic acid) was obtained similarly to Example 15 except that 700 mg of a 1 mass % aqueous solution of ascorbic acid described in Example 15 was changed to 21.0 mg of ascorbic acid (manufactured by BASF). It was confirmed that the concentration of dissolved oxygen being 0.01 ppm and the concentration of oxygen (less than 0.1 v/v %) of a container space did not change even in a sample during the preservation.

Example 17: Preparation of Injection Preparation (C-17)

A target injection preparation (C-17, 2.50 mass % of concentration of pemetrexed, 0.0054 mass % of concentration of a specific antioxidant agent in terms of ascorbic acid (0.01 mass % of concentration of trisodium ascorbyl phosphate)) was obtained similarly to Example 13 except that 5.0 mg of a 1 mass % aqueous solution of ascorbic acid described in Example 13 was changed to 50.0 mg of a 1 mass % aqueous solution of trisodium ascorbyl phosphate (manufactured by Wako Pure Chemical Industries, Ltd.). It was confirmed that the concentration of dissolved oxygen being 0.01 ppm and the concentration of oxygen (less than 0.1 v/v %) of a container space did not change even in a sample during the preservation.

Example 18: Preparation of Injection Preparation (C-18)

A target injection preparation (C-18, 2.50 mass % of concentration of pemetrexed, 0.01 mass % of concentration of ascorbic acid) was obtained similarly to Example 2 except that the concentration of oxygen described in Example 2 was changed to 0.1 v/v % to 0.2 v/v %. It was confirmed that the concentration of dissolved oxygen became 0.08 ppm and the concentration of oxygen of a container space became 0.1% to 0.2% even in a sample during the preservation.

Comparative Example 1: Preparation of Injection Preparation (R-1)

4.00 g of injection water (manufactured by Hikari Pharmaceutical Co., Ltd.), and pemetrexed disodium (125 mg as pemetrexed) were weighed into a clean 15 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residue was not recognized while performing external observation with the naked eye.

1 N hydrochloric acid (manufactured by Wako Pure Chemical Industries, Ltd.) was added to the prepared solution little by little and the pH value was adjusted to 7.0. Injection water was added thereto such that the total amount of the solution became 5.00 g.

The prepared solution was placed in a glove box, and nitrogen substitution was performed by stirring the solution for 2 hours at room temperature. Thereafter, the solution was sterilized and filtered using a 0.2 μm filter (made of PTFE) under nitrogen atmosphere (lower than or equal to 0.1 v/v % of oxygen concentration). Then, a vial (manufactured by Fuji Glass Co., Ltd., vial bottle 3010 Silicort) was filled with 1 mL of the sterilized and filtered solution. A target injection preparation (R-1, 2.50 mass % of concentration of pemetrexed) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., aluminum seal B (middle)) so as to cover the vial and the mouth of the rubber plug, and clamping the aluminum seal using a clipper from the above. It was confirmed that the concentration of dissolved oxygen being 0.01 ppm and the concentration of oxygen (less than 0.1 v/v %) of a container space did not change even in a sample during the preservation.

Comparative Example 2: Preparation of Injection Preparation (R-2)

4.00 g of injection water (manufactured by Hikari Pharmaceutical Co., Ltd.), 45.0 mg of a 1 mass % aqueous solution of thioglycerol (manufactured by Wako Pure Chemical Industries, Ltd., 3-mercapto-1,2-propanediol) which had been prepared in advance, 45.0 mg of disodium hydrogen phosphate (Wako Pure Chemical Industries, Ltd., "exclusive for production" of sodium hydrogen phosphate hydrate), and pemetrexed disodium (113 mg as pemetrexed) were weighed into a clean 15 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residue was not recognized while performing external observation with the naked eye.

1 N hydrochloric acid (manufactured by Wako Pure Chemical Industries, Ltd.) was added to the prepared solution little by little and the pH value was adjusted to 7.0. Injection water was added thereto such that the total amount of the solution became 4.50 g.

The prepared solution was placed in a glove box, and nitrogen substitution was performed by stirring the solution for 2 hours at room temperature. Thereafter, the solution was sterilized and filtered using a 0.2 μm filter (made of PTFE) under nitrogen atmosphere (lower than or equal to 0.1 v/v % of oxygen concentration). Then, a vial (manufactured by Fuji Glass Co., Ltd., vial bottle 3010 Silicort) was filled with 1 mL of the sterilized and filtered solution. A target injection preparation (R-2, 2.50 mass % of concentration of pemetrexed, 0.01 mass % of concentration of thioglycerol) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., aluminum seal B (middle)) so as to cover the vial and the mouth of the rubber plug, and clamping the aluminum seal using a clipper from the above. It was confirmed that the concentration of dissolved oxygen being 0.01 ppm and the concentration of oxygen (less than 0.1 v/v %) of a container space did not change even in a sample during the preservation.

Comparative Example 3: Preparation of Injection Preparation (R-3)

A target injection preparation (R-3, 2.50 mass % of concentration of pemetrexed, 1.00 mass % of concentration of ascorbic acid) was obtained similarly to Example 4 except that 45.0 mg of a 1 mass % aqueous solution of ascorbic acid (manufactured by BASF) described in Example 4 was changed to 45.0 mg of ascorbic acid (manufactured by BASF), and the pH described in Example 4 was changed from 7.0 to 7.2. It was confirmed that the concentration of dissolved oxygen being 0.01 ppm and the concentration of oxygen (less than 0.1 v/v %) of a container space did not change even in a sample during the preservation.

Comparative Example 4: Preparation of Injection Preparation (R-4)

A target injection preparation (R-4, 2.50 mass % of concentration of pemetrexed, 0.01 mass % of concentration of ascorbic acid) was obtained similarly to Example 2 except that the concentration of oxygen described in Example 2 was changed to 0.5 v/v % to 0.7 v/v %. It was confirmed that the concentration of dissolved oxygen being 0.01 ppm and the concentration of oxygen (less than 0.1 v/v %) of a container space did not change even in a sample during the preservation.

Comparative Example 5: Preparation of Injection Preparation (R-5)

30.0 g of injection water (manufactured by Hikari Pharmaceutical Co., Ltd.), 1.05 g of mannitol (Towa-Kasei Co., Ltd., Mannite P), and pemetrexed disodium (875 mg as pemetrexed) were weighed into a clean 110 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residue was not recognized while performing external observation with the naked eye.

1 N hydrochloric acid (manufactured by Wako Pure Chemical Industries, Ltd.) was added to the prepared solution little by little and the pH value was adjusted to 7.0. Injection water was added thereto such that the total amount of the solution became 35.0 g.

The prepared solution was sterilized and filtered using a 0.2 μm filter (made of PTFE). Then, a vial (manufactured by Fuji Glass Co., Ltd., vial bottle 3010 Silicort) was filled with 2 mL of the sterilized and filtered solution. A target injection preparation (R-5, 2.50 mass % of concentration of pemetrexed, 21.0 mass % of concentration of gaseous oxygen) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., aluminum seal B (middle)) so as to cover the vial and the mouth of the rubber plug, and clamping the aluminum seal using a clipper from the above. It was confirmed that the concentration of dissolved oxygen being 0.01 ppm and the concentration of oxygen (less than 0.1 v/v %) of a container space did not change even in a sample during the preservation.

Comparative Example 6: Preparation of Injection Preparation (R-6)

28.0 g of injection water (manufactured by Hikari Pharmaceutical Co., Ltd.), 1.05 g of mannitol (Towa-Kasei Co., Ltd., Mannite P), 350 mg of a 1 mass % aqueous solution of ascorbic acid (manufactured by DSM Nutrition Japan) which had been prepared in advance, and pemetrexed disodium (875 mg as pemetrexed) were weighed into a clean 110 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residue was not recognized while performing external observation with the naked eye.

1 N hydrochloric acid (manufactured by Wako Pure Chemical Industries, Ltd.) was added to the prepared solution little by little and the pH value was adjusted to 7.0. Injection water was added thereto such that the total amount of the solution became 35.0 g.

The prepared solution was sterilized and filtered using a 0.2 μm filter (made of PTFE). Then, a vial (manufactured by Fuji Glass Co., Ltd., vial bottle 3010 Silicort) was filled with 2 mL of the sterilized and filtered solution. A target injection preparation (R-6, 2.50 mass % of concentration of pemetrexed, 0.01 mass % of concentration of ascorbic acid, 21.0 mass % of concentration of gaseous oxygen) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., aluminum seal B (middle)) so as to cover the vial and the mouth of the rubber plug, and clamping the aluminum seal using a clipper from the above. It was confirmed that the concentration of dissolved oxygen being 8.11 ppm and 21.0% of concentration of oxygen of a container space did not change even in a sample during the preservation.

Comparative Example 7: Preparation of Injection Preparation (R-7)

A target injection preparation (R-7, 2.50 mass % of concentration of pemetrexed, 0.10 mass % of concentration of ascorbic acid) was obtained similarly to Comparative Example 6 except that the amount of mannitol described in Comparative Example 6 was changed to 980 mg, the amount of 1 mass % aqueous solution of ascorbic acid was changed to 3.50 g and 1 N hydrochloric acid was changed to 1 N sodium hydroxide (manufactured by Wako Pure Chemical Industries, Ltd.). It was confirmed that 8.11 ppm of concentration of dissolved oxygen and 21.0% of concentration of oxygen of a container space did not change even in a sample during the preservation.

Comparative Example 8: Preparation of Injection Preparation (R-8)

A target injection preparation (R-8, 2.50 mass % of concentration of pemetrexed, 1.00 mass % of concentration of ascorbic acid) was obtained similarly to Comparative Example 6 except that the amount of mannitol described in Comparative Example 6 was changed to 105 mg and the 1 mass % aqueous solution of ascorbic acid was changed to 350 mg of ascorbic acid (manufactured by DSM Nutrition Japan). It was confirmed that 8.11 ppm of concentration of dissolved oxygen and 21.0% of concentration of oxygen of a container space did not change even in a sample during the preservation.

The concentration of oxygen of gas in the container of each injection preparation was measured using the following measurement instrument. The measurement value is shown in Table 2. "–" in a composition in Table 2 represents non-formulation.

Measurement instrument: oxygen monitor OXY-1 (manufactured by Jikco Ltd.)

Measurement method: diaphragm-type galvanic cell type

As a specific measurement method, the concentration of oxygen in gas is measured by reading a display value of an oxygen monitor in the same space when producing an injection preparation.

As a device for measuring the concentration of dissolved oxygen in an aqueous composition contained in each injection preparation, InLab (registered trademark) SciencePro-ISM (manufactured by Mettler-Toledo International Inc.) was used. The concentration of dissolved oxygen was measured by bringing an electrode of the oxygen concentration determination device into contact with the aqueous composition contained in the injection preparation. The measurement value is shown in Table 2.

(Evaluation)

Among the obtained injection preparations, with respect to (C-1) to (C-18) and (R-1) to (R-3), each injection preparation which was placed in Lamizip (made of PET/AL) with Ageless (manufactured by Mitsubishi Gas Chemical Company, Inc., Z-100 PKC) and was subjected to heat sealing under nitrogen atmosphere (less than 0.1 v/v % of oxygen concentration in gas) was preserved in a thermostatic tank at 70° C. for 1 week to perform stress testing.

In addition, with respect to (R-4), each injection preparation which was placed in Lamizip (made of PET/AL) with Ageless (manufactured by Mitsubishi Gas Chemical Company, Inc., Z-100 PKC) and was subjected to heat sealing under nitrogen atmosphere (less than 0.5 v/v % of oxygen concentration in gas) was preserved in a thermostatic tank at 70° C. for 1 week to perform stress testing.

In addition, with respect to (R-5) to (R-8), each injection preparation was preserved in a thermostatic tank at 70° C. for 1 week to directly perform stress testing. Then, evaluation was performed through the method described below.

(1) Preservation Stability

A sample liquid after preservation was obtained after weighing about 10 mg of an injection preparation after preservation into a 1 mL volumetric flask, and diluting the injection preparation with Milli-Q water. Regarding an injection preparation before preservation, a sample before preservation was also obtained by preparing the injection preparation before preservation through the same method.

Quantitative determination of decomposition products of pemetrexed was performed using high performance liquid chromatograph. In the chromatograph detected in the following measurement condition, the quantitative determination of decomposition products was performed through quantitatively determining the amount of the maximum decomposition product in decomposition products at holding times of 3 minutes to 25 minutes. In addition, with respect to (C-1), (C-13), (C-14), (C-16), (R-1), and (R-3), the amount of decomposition product A at a holding time of 15 minutes and the amount of decomposition product B at a holding time of 20 minutes were quantitatively determined.

[HPLC Measurement Condition]

Detector: UV detector (detection wavelength: 230 nm)

Column: CapcellPak C-18, UG120, 4.6×150 mm, manufactured by Shiseido Japan Co., Ltd.

Column temperature: 25° C.

Development solvent: A: 0.1 vol % phosphoric acid aqueous solution

B: Acetonitrile

TABLE 1

| Development solvent composition: | |
|---|---|
| Time (minutes) | B Composition (%) |
| 0.01 | 10 |
| 25.00 | 16.25 |
| 25.01 | 70 |
| 35.00 | 70 |
| 35.01 | 10 |
| 45 | End |

Flow velocity: 1.5 mL/min

Temperature of sample cooler: 4° C.

Amount of injection: 5 μL

The preservation stability was evaluated as a proportion (%) of the amount of the maximum decomposition product in a sample liquid after preservation with respect to the amount of pemetrexed in a sample liquid before preservation by multiplying the area ratio by 100.

The evaluation results are shown in Tables 3 and 4 together with measurement values.

(2) Coloration of Injection Preparation

The coloration of an injection preparation after stress testing was quantitatively evaluated using a UV-visible spectrophotometer (manufactured by JASCO Corporation, V-630). Specifically, the absorbance at a wavelength of 420 nm was obtained by preparing a sample liquid which was obtained by diluting the injection preparation after stress testing with Milli-Q water by 10 times.

The evaluation of the coloration based on the absorbance was performed in accordance with the following criteria. The results are shown in Table 3.

A: less than 0.010
B: greater than or equal to 0.010 and less than 0.020
C: greater than or equal to 0.020

TABLE 2

| | Water-soluble preparation prescription Composition | | | | | | |
|---|---|---|---|---|---|---|---|
| | (i) Raw medicine | (ii) Antioxidant agent | | Another additive 1 | | Another additive 2 | |
| | Amount (mass %) | Type of additive | Amount (mass %) | Type of additive | Amount (mass %) | Type of additive | Amount (mass %) |
| Example 1 | 2.50 | Ascorbic acid | 0.01 | — | 0.00 | 1N hydrochloric acid | 0.01 |
| Example 2 | 2.50 | Ascorbic acid | 0.01 | Citric acid | 0.10 | 1N sodium hydroxide | 1.47 |
| Example 3 | 2.50 | Ascorbic acid | 0.01 | Citric acid | 1.00 | 1N sodium hydroxide | 13.74 |
| Example 4 | 2.50 | Ascorbic acid | 0.01 | Disodium hydrogen phosphate | 1.00 | 1N hydrochloric acid | 1.00 |
| Example 5 | 2.50 | Ascorbic acid | 0.01 | Disodium edetate | 0.01 | 1N hydrochloric acid | 0.08 |
| Example 6 | 2.50 | Ascorbic acid | 0.01 | Triethanolamine | 0.10 | 1N hydrochloric acid | 0.64 |
| Example 7 | 2.50 | Sodium ascorbate | 0.01 | Disodium hydrogen phosphate | 1.00 | 1N hydrochloric acid | 1.00 |
| Example 8 | 2.50 | Ascorbic acid | 0.01 | Trisodium citrate | 1.00 | 1N hydrochloric acid | 0.05 |
| Example 9 | 2.50 | Ascorbic acid | 0.01 | Trisodium citrate | 1.00 | 1N hydrochloric acid | 0.01 |
| Example 10 | 2.50 | Ascorbic acid | 0.01 | Trisodium citrate | 1.00 | 0.1N sodium hydroxide | 0.05 |
| Example 11 | 2.50 | Ascorbic acid | 0.01 | Trisodium citrate | 1.00 | 0.1N sodium hydroxide | 0.08 |
| Example 12 | 2.50 | Ascorbic acid | 0.01 | Trisodium citrate | 1.00 | 0.1N sodium hydroxide | 0.11 |
| Example 13 | 2.50 | Ascorbic acid | 0.001 | — | 0.00 | 1N hydrochloric acid | 0.06 |
| Example 14 | 2.50 | Ascorbic acid | 0.0001 | — | 0.00 | 1N hydrochloric acid | 0.05 |
| Example 15 | 2.50 | Ascorbic acid | 0.10 | — | 0.00 | 1N sodium hydroxide | 0.71 |
| Example 16 | 2.50 | Ascorbic acid | 0.30 | — | 0.00 | 1N sodium hydroxide | 1.64 |
| Example 17 | 2.50 | Trisodium ascorbyl phosphate | 0.01 | — | 0.00 | 1N hydrochloric acid | 0.08 |
| Example 18 | 2.50 | Ascorbic acid | 0.01 | Citric acid | 0.10 | 1N sodium hydroxide | 1.47 |
| Comparative Example 1 | 2.50 | — | 0.00 | — | 0.00 | 1N hydrochloric acid | 0.04 |
| Comparative Example 2 | 2.50 | Thioglycerol | 0.01 | Disodium hydrogen phosphate | 1.00 | 1N hydrochloric acid | 1.00 |
| Comparative Example 3 | 2.50 | Ascorbic acid | 1.00 | Disodium hydrogen phosphate | 1.00 | 1N sodium hydroxide | 5.00 |
| Comparative Example 4 | 2.50 | Ascorbic acid | 0.01 | Citric acid | 0.10 | 1N sodium hydroxide | 1.47 |
| Comparative Example 5 | 2.50 | — | 0.00 | Mannitol | 3.00 | 1N hydrochloric acid | 0.50 |
| Comparative Example 6 | 2.50 | Ascorbic acid | 0.01 | Mannitol | 3.00 | 1N hydrochloric acid | 0.13 |
| Comparative Example 7 | 2.50 | Ascorbic acid | 0.10 | Mannitol | 2.80 | 1N sodium hydroxide | 0.71 |
| Comparative Example 8 | 2.50 | Ascorbic acid | 1.00 | Mannitol | 1.00 | 1N sodium hydroxide | 5.89 |

| | Water-soluble preparation prescription | | | | |
|---|---|---|---|---|---|
| | Composition | | Specification | | |
| | (iii) Injection water Amount (mass %) | pH | Concentration of gaseous oxygen (v/v %) | Concentration of dissolved oxygen (ppm) | Number of oxygen molecules with respect to number of pemetrexed molecules |
| Example 1 | 97.5 | 7.0 | <0.1 | 0.01 | <0.00080 |
| Example 2 | 95.9 | 6.5 | <0.1 | 0.01 | <0.00080 |

TABLE 2-continued

|  | | | | |
|---|---|---|---|---|
| Example 3 | 82.8 | 6.5 | <0.1 | 0.01 | <0.00080 |
| Example 4 | 95.5 | 7.0 | <0.1 | 0.01 | <0.0023 |
| Example 5 | 97.4 | 7.0 | <0.1 | 0.01 | <0.0023 |
| Example 6 | 96.8 | 7.0 | <0.1 | 0.01 | <0.0023 |
| Example 7 | 95.5 | 7.0 | <0.1 | 0.01 | <0.0023 |
| Example 8 | 96.4 | 6.1 | <0.1 | 0.01 | <0.0025 |
| Example 9 | 96.5 | 6.6 | <0.1 | 0.01 | <0.0025 |
| Example 10 | 96.4 | 7.5 | <0.1 | 0.01 | <0.0025 |
| Example 11 | 96.4 | 8.0 | <0.1 | 0.01 | <0.0025 |
| Example 12 | 96.4 | 9.0 | <0.1 | 0.01 | <0.0023 |
| Example 13 | 97.4 | 7.0 | <0.1 | 0.01 | <0.0023 |
| Example 14 | 97.4 | 7.0 | <0.1 | 0.01 | <0.0023 |
| Example 15 | 96.7 | 7.0 | <0.1 | 0.01 | <0.0025 |
| Example 16 | 95.6 | 7.2 | <0.1 | 0.01 | <0.0025 |
| Example 17 | 97.4 | 7.0 | <0.1 | 0.01 | <0.0023 |
| Example 18 | 95.9 | 6.5 | 0.1 to 0.2 | 0.08 | 0.0016 to 0.0024 |
| Comparative Example 1 | 97.5 | 7.0 | <0.1 | 0.01 | <0.0023 |
| Comparative Example 2 | 95.5 | 7.0 | <0.1 | 0.01 | <0.0023 |
| Comparative Example 3 | 90.5 | 7.2 | <0.1 | 0.01 | <0.0023 |
| Comparative Example 4 | 95.9 | 6.5 | 0.5 to 0.7 | 0.01 | 0.0040 to 0.0048 |
| Comparative Example 5 | 94.0 | 7.0 | 21.0 | 8.11 | 0.168 |
| Comparative Example 6 | 94.4 | 7.0 | 21.0 | 8.11 | 0.168 |
| Comparative Example 7 | 93.9 | 7.0 | 21.0 | 8.11 | 0.168 |
| Comparative Example 8 | 89.6 | 7.0 | 21.0 | 8.11 | 0.168 |

TABLE 3

| | Evaluation result | |
|---|---|---|
| | Compound stability Maximum decomposition product Amount of decomposition product | Coloration Evaluation |
| Example 1 | 0.084% | A |
| Example 2 | 0.093% | A |
| Example 3 | 0.094% | A |
| Example 4 | 0.094% | A |
| Example 5 | 0.104% | A |
| Example 6 | 0.099% | A |
| Example 7 | 0.092% | A |
| Example 8 | 0.098% | A |
| Example 9 | 0.092% | A |
| Example 10 | 0.101% | A |
| Example 11 | 0.101% | A |
| Example 12 | 0.135% | A |
| Example 13 | 0.116% | A |
| Example 14 | 0.148% | A |
| Example 15 | 0.107% | A |
| Example 16 | 0.151% | A |
| Example 17 | 0.154% | A |
| Example 18 | 0.159% | A |
| Comparative Example 1 | 0.277% | A |
| Comparative Example 2 | 0.252% | A |
| Comparative Example 3 | 0.298% | B |
| Comparative Example 4 | 0.232% | C |
| Comparative Example 5 | 23.6% | C |
| Comparative Example 6 | 23.7% | C |
| Comparative Example 7 | 11.3% | C |
| Comparative Example 8 | 1.50% | C |

As is clear from the results of Table 3, it is possible to improve preservation stability of pemetrexed contained in an aqueous composition by adjusting the concentration of oxygen in gas within a container to be less than or equal to 0.2 volume % and by containing the aqueous composition which contains at least one antioxidant agent which is selected from the group consisting of ascorbic acid, an ascorbic acid derivative, and salts thereof, and the content of which is 0.0001 mass % to 0.5 mass % with respect to the total mass of the aqueous composition in terms of ascorbic acid. In addition, it is possible to suppress coloration of an injection preparation due to preservation with time.

Particularly, when (R-5), (R-7), and (R-8), cases in which the concentration of oxygen in gas is as high as 21.0 volume %, are compared, the amount of maximum decomposition product decreases depending on the amount of ascorbic acid added. In contrast, in the addition of ascorbic acid at 0.01 mass % (R-6), the effect of preservation stability is not expressed.

In contrast, it was found that the preservation stability was significantly improved compared to Comparative Example (R-1) without adding ascorbic acid even in a case where the amount of ascorbic acid added was 0.01 mass %, 0.001 mass %, and 0.0001 mass %, being low concentration, when comparing (C-1), (C-13), and (C-14) with (R-1) and (R-3)

under the condition of low concentration of oxygen in gas, being less than 0.1%. Moreover, it was found that in a case where the amount of ascorbic acid added is high as 1.0 mass %, the preservation stability is decreased compared to Comparative Example (R-3) without addition.

As is clear from the comparison of (C-1) with (R-2), it has not been found that addition of an antioxidant agent at a low concentration significantly improves preservation stability, in independent addition of thioglycerol of the antioxidant agent disclosed in JP2003-521518A (above-described Patent Document 1).

TABLE 4

|  | Evaluation result Compound stability | |
|---|---|---|
|  | Decomposition product A Amount of decomposition product | Decomposition product B Amount of decomposition product |
| Example 1 | 0.084% | 0.012% |
| Example 13 | 0.116% | 0.010% |
| Example 14 | 0.148% | 0.008% |
| Example 16 | 0.085% | 0.151% |
| Comparative Example 1 | 0.277% | 0.008% |
| Comparative Example 3 | 0.059% | 0.278% |

As is clear from the results of Table 4, the production amount of decomposition product A which is the maximum decomposition product in (R-1) is decreased in accordance with the amount of ascorbic acid added. In contrast, it was found that the production amount of decomposition product B increases if the amount of ascorbic acid added increases. As a result, it became clear that it was possible to improve the preservation stability of pemetrexed contained in the aqueous composition by adjusting the concentration of oxygen in gas within a container to be less than or equal to 0.2% and by containing the aqueous composition which contains an antioxidant agent of which the content is 0.0001 mass % to 0.5 mass % with respect to the total mass of the aqueous composition in terms of ascorbic acid.

Examples 19 to 21

Aqueous compositions of Examples 19 to 21 were obtained similarly to Example 1 except that the content of each component was changed to the amount described in Table 5.

Each vial bottle, in which the amount (ppm) of which of silicon eluted into water in a case where the container was filled with water and heat treatment was performed for 60 minutes at 121° C., indicated the elution amount described in Table 5 was prepared. Each vial bottle was filled with 1 mL of each of the obtained aqueous compositions (Examples 19 to 21) to obtain each injection preparation. Thereafter, each of the injection preparations was preserved at a temperature of 70° C. for 1 week to perform stress testing.

After performing the stress testing, the presence and absence of insoluble impurities in each of the injection preparations was evaluated through visual observation. A case where no insoluble impurity was confirmed through visual observation was set as A and a case where insoluble impurity was confirmed through visual observation was set as B. The results are shown in Table 6.

In addition, after performing the stress testing, the number of particles per 1 mL of insoluble fine particles (2 µm, 5 µm, 10 µm, and 25 µm) in each of the injection preparations was measured. The number of particles per 1 mL of the insoluble particles was measured using an in-liquid particulate measurement instrument (System 9703+ manufactured by Hach Company). Specifically, a sample liquid, which was obtained by diluting each of the injection preparations after the stress testing with injection water by 10 times, was prepared, and the number of particles in 5 mL of the sample liquid was measured and was substituted with the number of particles per 1 mL.

Regarding the presence and absence of insoluble impurities and the number of particles per 1 mL of insoluble fine particles in each of the injection preparations, the results are shown in Table 6.

TABLE 5

| | Container | | | | Composition | | | |
|---|---|---|---|---|---|---|---|---|
| | | | | Amount (ppm) of silicon eluted | (i) Raw medicine | (ii) antioxidant agent | | |
| | Type | Maker | Material | | Amount (mass %) | Type of additive | Amount (mass %) | |
| Example 19 | 3010 Silicort | Fuji Glass Co., Ltd. | Glass | 0.03 | 2.50 | Ascorbic acid | 0.01 | |
| Example 20 | Resin CZ | Daikyo Seiko. Ltd. | Resin | 0.01 | 2.50 | Ascorbic acid | 0.01 | |
| Example 21 | 3010 | Fuji Glass Co., Ltd. | Glass | 0.12 | 2.50 | Ascorbic acid | 0.01 | |

| | Composition | | | | | |
|---|---|---|---|---|---|---|
| | Another additive (1) | | Another additive (2) | | (iii) Injection water | |
| | Type of additive | Amount (mass %) | Type of additive | Amount (mass %) | Amount (mass %) | pH |
| Example 19 | Disodium hydrogen phosphate | 1.00 | 1N hydrochloric acid | 1.00 | 95.5 | 7.0 |

TABLE 5-continued

| | | | | | | |
|---|---|---|---|---|---|---|
| Example 20 | Disodium hydrogen phosphate | 1.00 | 1N hydrochloric acid | 1.00 | 95.5 | 7.0 |
| Example 21 | Disodium hydrogen phosphate | 1.00 | 1N hydrochloric acid | 1.00 | 95.5 | 7.0 |

TABLE 6

| | Evaluation result | | | | |
|---|---|---|---|---|---|
| | Insoluble Impurities | Insoluble fine particles | | | |
| | | 2 μm | 5 μm | 10 μm | 25 μm |
| Example 19 | A | 48.8 | 4.6 | 0.2 | 0.0 |
| Example 20 | A | 38.8 | 6.0 | 0.4 | 0.0 |
| Example 21 | A | 66.0 | 14.8 | 2.4 | 0.0 |

It became clear that, from the results of Table 6, it was possible to provide an injection preparation which can maintain preservation stability of pemetrexed to be high and can suppress production of insoluble impurities and insoluble fine particles even after the stress testing, using a container in which the amount of silicon eluted into water in a case where the container was filled with water and heat treatment was performed for 60 minutes at 121° C. was less than or equal to 1.0 ppm.

Example 22: Preparation of Injection Preparation (C-22)

18.0 g of injection water (manufactured by Hikari Pharmaceutical Co., Ltd.), 210 mg of a 1 mass % aqueous solution of ascorbic acid (manufactured by DSM Nutrition Japan) which had been prepared in advance, 21.0 mg of trisodium citrate (manufactured by Merck Millipore Corporation, trisodium citrate dihydrate), pemetrexed disodium (525 mg as pemetrexed), and 504 mg of a 1 mass % aqueous solution of cysteine hydrochloride (manufactured by Kyowa Hakko Bio Co., Ltd.) which had been prepared in advance were weighed into a clean 50 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residue was not recognized while performing external observation with the naked eye.

1 N (1 mol/L) hydrochloric acid was added to the prepared solution little by little and the pH value was adjusted to 6.5. Injection water was added thereto such that the total amount of the solution became 21.0 g.

The prepared solution was placed in a glove box, and nitrogen substitution in the solution was performed (at a concentration of dissolved oxygen of 0.01 ppm) by stirring the solution for 2 hours at room temperature. Thereafter, the solution was sterilized and filtered using a 0.2 μm filter (made of PTFE) under nitrogen atmosphere (0.5 v/v % to 0.6 v/v % of oxygen concentration). Then, a vial (manufactured by Fuji Glass Co., Ltd., vial bottle 3010 Silicort) was filled with 2 mL of the sterilized and filtered solution. A target second injection preparation (C-22, 2.50 mass % of concentration of pemetrexed, 0.01 mass % of concentration of ascorbic acid, 0.024 mass % of concentration of cysteine hydrochloride) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., aluminum seal B (middle)) so as to cover the vial and the mouth of the rubber plug, and clamping the aluminum seal using a clipper from the above.

Examples 23 to 38

Aqueous compositions (second aqueous compositions) of Examples 23 to 38 were obtained similarly to Example 22 except that the content of each component was changed to the amount described in Table 8. Each vial was filled with 1 mL of each of the aqueous compositions (Examples 23 to 38) to obtain each injection preparation (second injection preparations: C-23 to C-38). "–" in a composition in Table 8 represents non-formulation.

Comparative Example 9: Preparation of Injection Preparation (R-9)

18.0 g of injection water (manufactured by Hikari Pharmaceutical Co., Ltd.), 21.0 mg of trisodium citrate (manufactured by Merck Millipore Corporation, trisodium citrate dihydrate), pemetrexed disodium (525 mg as pemetrexed), and 210 mg of a 1 mass % aqueous solution of ascorbic acid (manufactured by DSM Nutrition Japan) were weighed into a clean 50 mL vial in which a stirrer was placed, and were stirred and dissolved for 10 minutes at room temperature. Determination as to whether or not the mixed solution became a homogeneous and clear solution was performed through visual observation. Specifically, it was determined that the dissolution was completed when dissolution residue was not recognized while performing external observation with the naked eye.

1 N (1 mol/L) hydrochloric acid was added to the prepared solution little by little and the pH value was adjusted to 6.5. Injection water was added thereto such that the total amount of the solution became 21.0 g.

The prepared solution was placed in a glove box, and nitrogen substitution was performed by stirring the solution for 2 hours at room temperature. Thereafter, the solution was sterilized and filtered using a 0.2 μm filter (made of PTFE) under nitrogen atmosphere (0.5 v/v % to 0.6 v/v % of oxygen concentration). Then, a vial (manufactured by Fuji Glass Co., Ltd., vial bottle 3010 Silicort) was filled with 2 mL of the sterilized and filtered solution. An injection preparation (R-9, 2.50 mass % of concentration of pemetrexed, 0.01 mass % of concentration of ascorbic acid) was obtained by tightly plugging the vial with a rubber plug (manufactured by Daikyo Seiko. Ltd.) which had been subjected to laminate coating, putting an aluminum seal (manufactured by Nichiden-Rika Glass Co., Ltd., aluminum seal B (middle)) so as to cover the vial and the mouth of the rubber plug, and clamping the aluminum seal using a clipper from the above.

Comparative Examples 10 to 13

Aqueous compositions (second aqueous compositions) of Comparative Examples 10 to 13 were obtained similarly to Comparative Example 9 except that the content of each component was changed to the amount described in Table 8. Each vial was filled with 1 mL of each of the aqueous compositions (Comparative Examples 10 to 13) to obtain each injection preparation (second injection preparations: C-10 to C-13).

The concentration of oxygen of gas in a container of each of the obtained injection preparations ((C-22) to (C-38) and (R-9) to (R-13)) was measured using the following measurement instrument. The measurement value is shown in Table 8.

Measurement instrument: oxygen monitor OXY-1 (manufactured by Jikco Ltd.)

Measurement method: diaphragm-type galvanic cell type

As a specific measurement method, the concentration of oxygen in gas is measured by reading a display value of an oxygen monitor in the same space when producing an injection preparation.

(Evaluation)

Among the obtained injection preparations, with respect to (C-22) to (C-38) and (R-9) to (R-13), each injection preparation which was placed in Lamizip (made of PET/AL) with Ageless (manufactured by Mitsubishi Gas Chemical Company, Inc., Z-100 PKC) and was subjected to heat sealing under nitrogen atmosphere (the concentration of oxygen in gas is a concentration of oxygen which is the same as that of a container space) was preserved in a thermostatic tank at 70° C. for 1 week to perform stress testing. Then, evaluation was performed through the method described below.

(1) Preservation Stability

A sample liquid after preservation was obtained after weighing about 10 mg of an injection preparation after preservation into a 1 mL volumetric flask, and diluting the injection preparation with Milli-Q water. Regarding an injection preparation before preservation, a sample before preservation was also obtained by preparing the injection preparation before preservation through the same method.

Quantitative determination of decomposition products of pemetrexed was performed using high performance liquid chromatograph. In the chromatograph detected in the following measurement condition, the amount of the maximum decomposition product in decomposition products at holding times of 3 minutes to 25 minutes was quantitatively determined.

[HPLC Measurement Condition]

Detector: UV detector (detection wavelength: 230 nm)

Column: CapcellPak C-18, UG120, 4.6×150 mm, manufactured by Shiseido Japan Co., Ltd.

Column temperature: 25° C.

Development solvent: A: 0.1 vol % phosphoric acid aqueous solution

B: Acetonitrile

TABLE 7

| Development solvent composition: | |
|---|---|
| Time (minutes) | B Composition (%) |
| 0.01 | 10 |
| 25.00 | 16.25 |
| 25.01 | 70 |
| 35.00 | 70 |
| 35.01 | 10 |
| 45 | End |

Flow velocity: 1.5 mL/min

Temperature of sample cooler: 4° C.

Amount of injection: 5 μL

The preservation stability was evaluated as a proportion (%) of the amount of the maximum decomposition product in a sample liquid after preservation with respect to the amount of pemetrexed in a sample liquid before preservation by multiplying the area ratio by 100.

In addition, the evaluation of suppressing decomposition based on the amount of the maximum decomposition product was performed in accordance with the following criteria. The results are shown in Table 8.

AA: Less than 0.04%

A: Greater than or equal to 0.04% and less than 0.07%

B: Greater than or equal to 0.07% and less than 0.18%

C: Greater than or equal to 0.18%

The evaluation results are shown in Table 8 together with measurement values.

(2) Coloration of Injection Preparation

The coloration of an injection preparation after stress testing was quantitatively evaluated using a UV-visible spectrophotometer (manufactured by JASCO Corporation, V-630). Specifically, the absorbance at a wavelength of 420 nm was obtained by preparing a sample liquid which was obtained by diluting the injection preparation after stress testing with Milli-Q water by 10 times.

The evaluation of the coloration based on the absorbance was performed in accordance with the following criteria. The results are shown in Table 8.

AA: Less than 0.002

A: Greater than or equal to 0.002 and less than 0.010

B: Greater than or equal to 0.010 and less than 0.020

C: Greater than or equal to 0.020

(3) Comprehensive Evaluation

Comprehensive evaluation was performed in accordance with the following evaluation criteria.

AA: Both of the evaluation of preservation stability and the evaluation of coloration are AA, or any one of the evaluation of preservation stability and the evaluation of coloration is AA and the other one is A.

A: Both of the evaluation of preservation stability and the evaluation of coloration are A.

B: Both of the evaluation of preservation stability and the evaluation of coloration are B, or any one of the evaluation of preservation stability and the evaluation of coloration is A or AA and the other one is B.

C: Any one of the evaluation of preservation stability and the evaluation of coloration is B and the other one is C.

D: Both of the evaluation of preservation stability and the evaluation of coloration are C.

TABLE 8

| | Prescription | | | | | |
|---|---|---|---|---|---|---|
| | Pemetrexed (mass %) | Ascorbic acid (mass %) | Cysteine hydrochloride (mass %) | Another additive | Trisodium citrate (mass %) | pH |
| Example 22 | 2.50 | 0.01 | 0.024 | — | 0.10 | 6.5 |
| Example 23 | 2.50 | 0.03 | 0.02 | — | 0.10 | 7.0 |
| Example 24 | 2.50 | 0.10 | 0.02 | — | 0.10 | 7.0 |
| Example 25 | 2.50 | 0.10 | 0.02 | — | 0.10 | 6.0 |
| Example 26 | 2.50 | 0.01 | 0.02 | — | 0.10 | 7.0 |
| Example 27 | 2.50 | 0.01 | 0.02 | — | 0.10 | 7.9 |
| Example 28 | 2.50 | 0.01 | 0.02 | — | 0.10 | 9.2 |
| Example 29 | 2.50 | 0.01 | 0.05 | — | 0.10 | 6.5 |
| Example 30 | 2.50 | 0.01 | 0.10 | — | 0.10 | 6.5 |
| Example 31 | 2.50 | 0.01 | 0.01 | — | 0.10 | 6.5 |
| Example 32 | 2.50 | 0.01 | 0.005 | — | 0.10 | 6.5 |
| Example 33-1 | 2.50 | 0.01 | 0.002 | — | 0.10 | 6.5 |
| Example 33-2 | 2.50 | 0.01 | 0.0005 | — | 0.10 | 6.5 |
| Example 34 | 2.50 | 0.01 | 0.00 | Thioglycerol (0.036%) | 0.10 | 6.5 |
| Example 35 | 2.50 | 0.01 | 0.02 | — | 0.10 | 6.5 |
| Example 36 | 2.50 | 0.01 | 0.02 | — | 0.10 | 6.5 |
| Example 37 | 2.50 | 0.01 | 0.02 | — | 0.10 | 6.5 |
| Example 38 | 2.50 | 0.10 | 0.02 | — | 0.10 | 6.0 |
| Comparative Example 9 | 2.50 | 0.01 | 0.00 | — | 0.10 | 6.5 |
| Comparative Example 10 | 2.50 | 0.00 | 0.00 | — | 0.10 | 6.5 |
| Comparative Example 11 | 2.50 | 0.00 | 0.02 | — | 0.10 | 6.5 |
| Comparative Example 12 | 2.50 | 0.00 | 0.02 | — | 0.10 | 9.2 |
| Comparative Example 13 | 2.50 | 0.01 | 0.02 | — | 0.10 | 6.5 |

| | Prescription | | Result (70° C. for 1 week) | | |
|---|---|---|---|---|---|
| | Concentration of gaseous oxygen (volume %) | Number of oxygen molecules with respect to number of pemetrexed molecules | Amount of maximum decomposition product (%) | Coloration | Comprehensive evaluation |
| Example 22 | 0.5 to 0.6 | 0.0040 to 0.0048 | 0.065 A | 0.005 A | A |
| Example 23 | 0.5 to 0.6 | 0.0040 to 0.0048 | 0.063 A | 0.005 A | A |
| Example 24 | 0.5 to 0.6 | 0.0040 to 0.0048 | 0.058 A | 0.007 A | A |
| Example 25 | 0.5 to 0.6 | 0.0040 to 0.0048 | 0.078 B | 0.009 A | B |
| Example 26 | 0.5 to 0.6 | 0.0040 to 0.0048 | 0.042 A | 0.009 A | A |
| Example 27 | 0.5 to 0.6 | 0.0040 to 0.0048 | 0.027 AA | 0.008 A | AA |
| Example 28 | 0.5 to 0.6 | 0.0040 to 0.0048 | 0.019 AA | 0.011 B | B |
| Example 29 | 0.5 to 0.6 | 0.0040 to 0.0048 | 0.053 A | 0.005 A | A |
| Example 30 | 0.5 to 0.6 | 0.0040 to 0.0048 | 0.053 A | 0.002 A | A |
| Example 31 | 0.5 to 0.6 | 0.0040 to 0.0048 | 0.120 B | 0.007 A | B |
| Example 32 | 0.5 to 0.6 | 0.0040 to 0.0048 | 0.135 B | 0.009 A | B |
| Example 33-1 | 0.5 to 0.6 | 0.0040 to 0.0048 | 0.143 B | 0.014 B | B |
| Example 33-2 | 0.5 to 0.6 | 0.0040 to 0.0048 | 0.145 B | 0.020 B | B |
| Example 34 | 0.5 to 0.6 | 0.0040 to 0.0048 | 0.138 B | 0.004 A | B |
| Example 35 | 0.7 to 0.8 | 0.0056 to 0.0064 | 0.104 B | 0.009 A | B |
| Example 36 | 0.9 to 1.0 | 0.0072 to 0.0080 | 0.124 B | 0.010 B | B |
| Example 37 | 1.1 to 1.2 | 0.0088 to 0.0096 | 0.148 B | 0.010 B | B |

TABLE 8-continued

| | | | | | |
|---|---|---|---|---|---|
| Example 38 | 1.3 to 1.4 | 0.010 to 0.011 | 0.173 B | 0.016 B | B |
| Comparative Example 9 | 0.5 to 0.6 | 0.0056 to 0.0064 | 0.111 B | 0.023 C | C |
| Comparative Example 10 | 0.5 to 0.6 | 0.0056 to 0.0064 | 0.240 C | 0.014 B | C |
| Comparative Example 11 | 0.5 to 0.6 | 0.0056 to 0.0064 | 0.194 C | 0.010 B | C |
| Comparative Example 12 | 0.5 to 0.6 | 0.0056 to 0.0064 | 0.074 B | 0.026 C | C |
| Comparative Example 13 | 2.0 to 2.2 | 0.016 to 0.018 | 0.434 C | 0.027 C | D |

It became clear from the results described in Table 8 that the present invention can exhibit the effect of suppressing decomposition of pemetrexed or a salt thereof contained in an aqueous composition and suppressing coloration of an injection preparation in a case where a second aqueous composition contains a specific amount of an antioxidant agent A and a specific amount of an antioxidant agent B, and the concentration of oxygen in gas within a container which encloses the second aqueous composition is less than or equal to 1.5 volume %.

Examples 39 to 53

Injection preparations C-39 to C-53 in Examples 39 to 53 were obtained similarly to the injection preparation C-22 in Example 22 except that the type and the content of each component were changed to the type of the content thereof described in Table 9. Regarding each of the obtained injection preparations C-39 to C-53, each evaluation of (1) preservation stability, (2) coloration of an injection preparation, and (3) comprehensive evaluation was performed similarly to the injection preparation C-22 in Example 22. The results are shown in Table 9.

TABLE 9

| | Prescription | | | | | | |
|---|---|---|---|---|---|---|---|
| | Pemetrexed (mass %) | Ascorbic acid (mass %) | Cysteine hydrochloride (mass %) | Thioglycerol (mass %) | Trisodium citrate (mass %) | Mannitol (mass %) | pH |
| Example 39 | 2.50 | 0.01 | 0.024 | 0.036 | 0.10 | 2.70 | 7.8 |
| Example 40 | 2.50 | 0.05 | 0.024 | 0.036 | 0.10 | 2.70 | 7.8 |
| Example 41 | 2.50 | 0.10 | 0.024 | 0.036 | 0.10 | 2.70 | 7.8 |
| Example 42 | 2.50 | 0.30 | 0.024 | 0.036 | 0.10 | 2.70 | 7.8 |
| Example 43 | 2.50 | 1.00 | 0.024 | 0.036 | 0.10 | 2.70 | 7.8 |
| Example 44 | 2.50 | 0.05 | 0.024 | 0.036 | 0.10 | 2.70 | 6.5 |
| Example 45 | 2.50 | 0.10 | 0.024 | 0.036 | 0.10 | 2.70 | 6.5 |
| Example 46 | 2.50 | 0.30 | 0.024 | 0.036 | 0.10 | 2.70 | 6.5 |
| Example 47 | 2.50 | 0.01 | 0.024 | 0.036 | 0.10 | 2.70 | 7.8 |
| Example 48 | 2.50 | 0.01 | 0.051 | 0.036 | 0.10 | 2.70 | 7.8 |
| Example 49 | 2.50 | 0.01 | 0.051 | 0.076 | 0.10 | 2.70 | 7.8 |
| Example 50 | 2.50 | 0.05 | 0.051 | 0.076 | 0.10 | 2.70 | 7.8 |
| Example 51 | 2.50 | 0.10 | 0.051 | 0.076 | 0.10 | 2.70 | 7.8 |
| Example 52 | 2.50 | 0.30 | 0.051 | 0.076 | 0.10 | 2.70 | 7.8 |
| Example 53 | 2.50 | 1.00 | 0.051 | 0.076 | 0.10 | 2.70 | 7.8 |

| | Prescription | | Result (70° C. for 1 week) | | |
|---|---|---|---|---|---|
| | Concentration of gaseous oxygen (volume %) | Number of oxygen molecules with respect to number of pemetrexed molecules | Amount of maximum decomposition product (%) | Coloration | Comprehensive evaluation |
| Example 39 | 1.0 to 1.1 | 0.0080 to 0.0088 | 0.043 A | 0.002 A | A |
| Example 40 | 1.0 to 1.1 | 0.0080 to 0.0088 | 0.035 AA | 0.001 AA | AA |
| Example 41 | 1.0 to 1.1 | 0.0080 to 0.0088 | 0.036 AA | 0.003 A | AA |
| Example 42 | 1.0 to 1.1 | 0.0080 to 0.0088 | 0.042 A | 0.006 A | A |
| Example 43 | 1.0 to 1.1 | 0.0080 to 0.0088 | 0.046 A | 0.008 A | A |
| Example 44 | 1.0 to 1.1 | 0.0080 to 0.0088 | 0.059 A | 0.005 A | A |
| Example 45 | 1.0 to 1.1 | 0.0080 to 0.0088 | 0.062 A | 0.005 A | A |
| Example 46 | 1.0 to 1.1 | 0.0080 to 0.0088 | 0.065 A | 0.007 A | A |

TABLE 9-continued

| | | | | | |
|---|---|---|---|---|---|
| Example 47 | 1.0 to 1.1 | 0.0080 to 0.0088 | 0.043 A | 0.002 A | A |
| Example 48 | 1.0 to 1.1 | 0.0080 to 0.0088 | 0.037 AA | 0.002 A | AA |
| Example 49 | 1.0 to 1.1 | 0.0080 to 0.0088 | 0.045 A | 0.001 AA | AA |
| Example 50 | 1.0 to 1.1 | 0.0080 to 0.0088 | 0.041 A | 0.002 A | A |
| Example 51 | 1.0 to 1.1 | 0.0080 to 0.0088 | 0.041 A | 0.002 A | A |
| Example 52 | 1.0 to 1.1 | 0.0080 to 0.0088 | 0.042 A | 0.002 A | A |
| Example 53 | 1.0 to 1.1 | 0.0080 to 0.0088 | 0.041 A | 0.002 A | A |

Reference Examples 1 to 3

Each injection preparation of Reference Examples 1 to 3 was obtained similarly to Example 22 except that the content of each component was changed to the amount described in Table 10 and the concentration of oxygen in gas within a container of the obtained injection preparation was changed to the amount described in Table 10.

Thereafter, each of the injection preparations was preserved at a temperature of 70° C. for 1 week to perform stress testing.

After performing the stress testing, the presence and absence of insoluble impurities in each of the injection preparations was evaluated through visual observation.

A case where no insoluble impurity was confirmed through visual observation was set as "++" and a case where insoluble impurity was confirmed through visual observation but was in a level which does not cause a problem was set as "+". The results are shown in Table 10.

TABLE 10

| | Prescription | | | | | | | Result |
|---|---|---|---|---|---|---|---|---|
| | Pemetrexed (mass %) | Ascorbic acid (mass %) | Cysteine hydrochloride (mass %) | Trisodium citrate (mass %) | pH | Concentration of gaseous oxygen (volume %) | Number of oxygen molecules with respect to number of pemetrexed molecules | (70° C. for 1 week) Insoluble impurities |
| Reference Example 1 | 2.50 | 0.01 | 0.20 | 0.10 | 7.0 | 0.5 to 0.6 | 0.0040 to 0.0048 | ++ |
| Reference Example 2 | 2.50 | 0.01 | 0.00 | 0.10 | 7.0 | <0.1 | <0.00080 | ++ |
| Reference Example 3 | 2.5 | 0.01 | 0 | 0 | 7.0 | <0.1 | <0.00080 | + |

It became clear from the results of Table 10 that it is possible to prepare an injection preparation which can suppress generation of insoluble impurities which can be generated during preservation, by containing citric acid or a salt thereof as a pH modifier.

The disclosures of JP2013-208351, filed Oct. 3, 2013, JP2013-246565, filed Nov. 28, 2013, and JP2014-072126, filed Mar. 31, 2014 are incorporated in the present specification for reference.

All of the documents, patent applications, and technical standards described in the present specification are incorporated in the present specification for reference to the same extent as a case where incorporation of individual document, patent application, and technical standard for reference is specifically and individually stated.

What is claimed is:

1. An injection preparation comprising:
an aqueous composition containing the following (i) to (iv); and
a container which encloses the aqueous composition,
wherein the concentration of oxygen in gas within the container which encloses the aqueous composition is less than or equal to 1.5 volume %:
(i) pemetrexed or a salt thereof;
(ii) at least one antioxidant agent A which is at least one selected from the group consisting of ascorbic acid, trisodium ascorbyl phosphate, and sodium ascorbate, and the content of which is 0.001 mass % to 1.0 mass % with respect to the total mass of the aqueous composition in terms of ascorbic acid;
(iii) at least one antioxidant agent B which is at least one selected from the group consisting of cysteine, a salt thereof, and thioglycerol, and the content of which is 0.00050 mass % to 0.15 mass % with respect to the total mass of the aqueous composition; and
(iv) an aqueous solvent of greater than or equal to 50 mass % with respect to the total mass of the aqueous composition.

2. An injection preparation comprising:
an aqueous composition; and
a container which encloses the aqueous composition,
wherein the aqueous composition contains the following (i) to (iv), and
wherein the ratio of the number of oxygen molecules with respect to the number of pemetrexed molecules in the injection preparation is less than or equal to 0.0120:
(i) pemetrexed or a salt thereof;
(ii) at least one antioxidant agent A which is at least one selected from the group consisting of ascorbic acid, trisodium ascorbyl phosphate, and sodium ascorbate, and the content of which is 0.001 mass % to 1.0 mass % with respect to the total mass of the aqueous composition in terms of ascorbic acid;
(iii) at least one antioxidant agent B which is at least one selected from the group consisting of cysteine, a salt thereof, and thioglycerol, and the content of which is 0.00050 mass % to 0.15 mass % with respect to the total mass of the aqueous composition; and (iv) an aqueous solvent of greater than or equal to 50 mass % with respect to the total mass of the aqueous composition.

3. The injection preparation according to claim 1, wherein the at least one antioxidant agent B includes cysteine or a salt thereof.

4. The injection preparation according to claim 1, wherein the at least one antioxidant agent B includes cysteine or a salt thereof, and thioglycerol.

5. The injection preparation according to claim 1, wherein the content of the antioxidant agent A is 0.005 mass % to 0.5 mass % with respect to the total mass of the aqueous composition.

6. The injection preparation according to claim 1, wherein the content of the antioxidant agent B is 0.0050 mass % to 0.15 mass % with respect to the total mass of the aqueous composition.

7. The injection preparation according to claim 1, wherein the ratio of the content of the antioxidant agent A to the content of the antioxidant agent B is 1:0.05 to 1:10 on a mass basis.

8. The injection preparation according to claim 1, wherein the pH of the aqueous composition is higher than 5.5 and less than or equal to 9.5.

9. The injection preparation according to claim 1, wherein the aqueous composition contains at least one pH modifier selected from the group consisting of hydrochloric acid, sodium hydroxide, phosphoric acid or a salt thereof, citric acid or a salt thereof, triethanolamine, trometamol, and disodium edetate.

10. The injection preparation according to claim 9, wherein the pH modifier is at least one selected from citric acid or a salt thereof.

11. A method for producing an injection preparation, comprising:

producing an aqueous composition which contains:

(i) pemetrexed or a salt thereof, (ii) at least one antioxidant agent A which is at least one selected from the group consisting of ascorbic acid, trisodium ascorbyl phosphate, and sodium ascorbate, and the content of which is 0.001 mass % to 1.0 mass % with respect to the total mass of the aqueous composition in terms of ascorbic acid;

(iii) at least one antioxidant agent B which is at least one selected from the group consisting of cysteine, a salt thereof, and thioglycerol, and the content of which is 0.00050 mass % to 0.15 mass % with respect to the total mass of the aqueous composition; and (iv) an aqueous solvent of greater than or equal to 50 mass % with respect to the total mass of the aqueous composition; and filling a container with the aqueous composition under an inert gas atmosphere or substituting gas within the container with inert gas after filling the container with the aqueous composition.

12. The production method according to claim 11, wherein the inert gas is nitrogen.

* * * * *